(12) United States Patent
Heil et al.

(10) Patent No.: US 11,869,649 B2
(45) Date of Patent: Jan. 9, 2024

(54) UNIVERSAL INTERFACE OPERABLE WITH MULTIPLE PATIENT SUPPORT APPARATUSES

(71) Applicant: Hill-Rom Services, Inc., Batesville, IN (US)

(72) Inventors: Thomas F. Heil, Batesville, IN (US); Eric D. Agdeppa, Cincinnati, OH (US); Steven A. Dixon, Riverview, FL (US); Charles A. Howell, Knoxville, TN (US); Thomas M. Gillis, Cincinnati, OH (US); Keith A. Huster, Sunman, IN (US); Irvin J. Vanderpohl, III, Greensburg, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 613 days.

(21) Appl. No.: 16/654,252

(22) Filed: Oct. 16, 2019

(65) Prior Publication Data
US 2020/0050750 A1    Feb. 13, 2020

Related U.S. Application Data

(63) Continuation of application No. 14/501,380, filed on Sep. 30, 2014, now Pat. No. 10,474,808, which is a
(Continued)

(51) Int. Cl.
*G16H 40/67* (2018.01)
*G16H 20/17* (2018.01)
(Continued)

(52) U.S. Cl.
CPC ............. *G16H 20/17* (2018.01); *G06F 21/44* (2013.01); *G06Q 10/063* (2013.01);
(Continued)

(58) Field of Classification Search
CPC ......... G16H 10/60; G16H 40/63; G16H 40/67
(Continued)

(56) References Cited

U.S. PATENT DOCUMENTS 3,643,219 A    2/1972   Heimann
3,910,659 A    10/1975  Peterson
(Continued)

FOREIGN PATENT DOCUMENTS

EP    0168158 A2    1/1986
EP    0376066 A1    7/1990
(Continued)

OTHER PUBLICATIONS

Peng, Shih-Wei, Feng-Li Lian, and Li-Chen Fu, "Mechanism design and mechatronic control of a multifunctional test bed for bedridden healthcare." IEEE/ASME transactions on mechatronics 15.2 (2009):234-241.
(Continued)

*Primary Examiner* — Mark Holcomb
(74) *Attorney, Agent, or Firm* — Barnes & Thornburg LLP

(57) ABSTRACT

A care system includes a mobile communication device, a remote server, and a patient support system that is in communication with either or both of the mobile communication device and the remote server. The mobile communication device may operate as a user interface for the patient support system. The remote server may provide computing power for the patient support system for resource intensive computing tasks.

23 Claims, 9 Drawing Sheets

Related U.S. Application Data continuation-in-part of application No. 14/223,355, filed on Mar. 24, 2014, now Pat. No. 10,290,071.

(60) Provisional application No. 61/806,556, filed on Mar. 29, 2013, provisional application No. 61/806,771, filed on Mar. 29, 2013.

(51) Int. Cl.
| | |
|---|---|
| *G06F 21/44* | (2013.01) |
| *H04L 9/40* | (2022.01) |
| *G16H 40/63* | (2018.01) |
| *G06Q 10/063* | (2023.01) |
| *G16H 10/60* | (2018.01) |

(52) U.S. Cl.
CPC ............ *G16H 10/60* (2018.01); *G16H 40/63* (2018.01); *G16H 40/67* (2018.01); *H04L 63/08* (2013.01); *H04L 63/10* (2013.01)

(58) Field of Classification Search
USPC .......................................................... 705/2
See application file for complete search history.

(56) References Cited

U.S. PATENT DOCUMENTS

| | | |
|---|---|---|
| 3,946,159 A | 3/1976 | Fay |
| 4,356,475 A | 10/1982 | Neumann et al. |
| 4,410,158 A | 10/1983 | Maffei |
| 4,452,499 A | 6/1984 | Verburg |
| 4,489,454 A | 12/1984 | Thompson |
| 4,557,453 A | 12/1985 | McCloskey |
| 4,584,989 A | 4/1986 | Stith |
| 4,607,897 A | 8/1986 | Schwartz |
| 4,687,167 A | 8/1987 | Skalka et al. |
| 4,708,312 A | 11/1987 | Rohr |
| 4,640,485 A | 12/1987 | Day et al. |
| 4,715,385 A | 12/1987 | Cudahy et al. |
| 4,724,555 A | 2/1988 | Poehner et al. |
| 4,738,369 A | 4/1988 | Desjardins |
| 4,747,172 A | 5/1988 | Hohol et al. |
| 4,756,706 A | 7/1988 | Kerns et al. |
| 4,768,241 A | 9/1988 | Beney |
| 4,783,036 A | 11/1988 | Vossoughi |
| 4,835,372 A | 5/1989 | Gombrich et al. |
| 4,836,478 A | 6/1989 | Sweere |
| 4,848,710 A | 7/1989 | Newman |
| 4,852,500 A | 8/1989 | Ryburg et al. |
| 4,857,713 A | 8/1989 | Brown |
| 4,872,679 A | 10/1989 | Bohaski et al. |
| 4,890,856 A | 1/1990 | Mursch et al. |
| 4,934,933 A | 6/1990 | Fuchs |
| 4,945,592 A | 8/1990 | Sims et al. |
| 4,981,139 A | 1/1991 | Pfohl |
| 4,993,683 A | 2/1991 | Kreuzer |
| 5,023,967 A | 6/1991 | Ferrand |
| 5,036,852 A | 8/1991 | Leishman |
| 5,072,906 A | 12/1991 | Foster |
| 5,077,843 A | 1/1992 | Foster et al. |
| 5,108,063 A | 4/1992 | Koerber, Sr. et al. |
| 5,117,521 A | 6/1992 | Foster et al. |
| 5,187,641 A | 2/1993 | Muskatello et al. |
| 5,272,318 A | 12/1993 | Gorman |
| 5,284,255 A | 2/1994 | Foster et al. |
| 5,319,816 A | 6/1994 | Ruehl |
| 5,330,415 A | 7/1994 | Storti et al. |
| 5,335,651 A | 8/1994 | Foster et al. |
| 5,337,845 A | 8/1994 | Foster et al. |
| 5,357,396 A | 10/1994 | Alm |
| 5,362,021 A | 11/1994 | Phillips |
| 5,375,604 A | 12/1994 | Kelly et al. |
| 5,377,371 A | 1/1995 | Foster |
| 5,396,673 A | 3/1995 | Foster |
| 5,398,359 A | 3/1995 | Foster |
| 5,400,991 A | 3/1995 | Werner |
| 5,407,163 A | 4/1995 | Kramer et al. |
| 5,417,222 A | 5/1995 | Dempsey et al. |
| 5,455,851 A | 10/1995 | Chaco et al. |
| 5,455,975 A | 10/1995 | Foster |
| 5,457,831 A | 10/1995 | Foster et al. |
| 5,473,536 A | 12/1995 | Wimmer |
| 5,473,997 A | 12/1995 | Solomon et al. |
| 5,494,051 A | 2/1996 | Schneider, Sr. |
| 5,497,766 A | 3/1996 | Foster et al. |
| 5,502,480 A | 3/1996 | Kuga et al. |
| 5,513,406 A | 5/1996 | Foster et al. |
| 5,527,289 A | 6/1996 | Foster et al. |
| 5,536,084 A | 7/1996 | Curtis et al. |
| 5,542,138 A | 8/1996 | Williams et al. |
| 5,544,649 A | 8/1996 | David et al. |
| 5,556,065 A | 9/1996 | Wadley |
| 5,561,412 A | 10/1996 | Novak et al. |
| 5,562,091 A | 10/1996 | Foster et al. |
| 5,579,001 A | 11/1996 | Dempsey et al. |
| 5,579,775 A | 12/1996 | Dempsey et al. |
| 5,618,090 A | 4/1997 | Montague et al. |
| 5,623,925 A | 4/1997 | Swenson et al. |
| 5,630,566 A | 5/1997 | Case |
| 5,640,953 A | 6/1997 | Bishop et al. |
| 5,647,491 A | 7/1997 | Foster et al. |
| 5,651,775 A | 7/1997 | Walker et al. |
| 5,664,270 A | 9/1997 | Bell et al. |
| 5,687,717 A | 11/1997 | Halpern et al. |
| 5,699,038 A | 12/1997 | Ulrich et al. |
| 5,712,482 A | 1/1998 | Gaiser et al. |
| 5,715,138 A | 2/1998 | Choi |
| 5,732,401 A | 3/1998 | Conway |
| 5,732,712 A | 3/1998 | Adair |
| 5,738,102 A | 4/1998 | Lemelson |
| 5,738,316 A | 4/1998 | Sweere et al. |
| 5,743,503 A | 4/1998 | Voeller et al. |
| 5,749,374 A | 5/1998 | Schneider, Sr. |
| 5,752,917 A | 5/1998 | Fuchs |
| 5,769,440 A | 6/1998 | Jones |
| 5,771,511 A | 6/1998 | Kummer et al. |
| 5,772,585 A | 6/1998 | Lavin et al. |
| 5,772,599 A | 6/1998 | Nevo et al. |
| 5,788,851 A | 8/1998 | Kenley et al. |
| 5,791,263 A | 8/1998 | Watt et al. |
| 5,799,917 A | 9/1998 | Li |
| 5,820,623 A | 10/1998 | Ng |
| 5,822,544 A | 10/1998 | Chaco et al. |
| 5,826,846 A | 10/1998 | Buccieri et al. |
| 5,831,816 A | 11/1998 | Johns et al. |
| 5,838,223 A | 11/1998 | Gallant et al. |
| 5,842,672 A | 12/1998 | Sweere et al. |
| 5,876,008 A | 3/1999 | Sweere et al. |
| 5,883,370 A | 3/1999 | Walker et al. |
| 5,889,568 A | 3/1999 | Seraphim et al. |
| 5,895,354 A | 4/1999 | Simmons |
| 5,895,571 A | 4/1999 | Utterberg |
| 5,898,961 A | 5/1999 | Ambach et al. |
| 5,903,211 A | 5/1999 | Flego et al. |
| 5,907,291 A | 5/1999 | Chen et al. |
| 5,918,328 A | 7/1999 | Ramsey |
| 5,918,331 A | 7/1999 | Hall et al. |
| 5,918,841 A | 7/1999 | Sweere et al. |
| 5,924,665 A | 7/1999 | Sweere et al. |
| 5,944,659 A | 8/1999 | Flach et al. |
| 5,947,429 A | 9/1999 | Sweere et al. |
| 5,957,838 A | 9/1999 | Rantala |
| 5,960,085 A | 9/1999 | de la Huerga |
| 5,961,448 A | 10/1999 | Swenson et al. |
| 5,966,760 A | 10/1999 | Gallant et al. |
| 5,973,598 A | 10/1999 | Beigel |
| 5,975,081 A | 11/1999 | Hood et al. |
| 5,978,211 A | 11/1999 | Hong |
| 5,991,947 A | 11/1999 | Lavin et al. |
| 5,992,809 A | 11/1999 | Sweere et al. |
| 5,993,006 A | 11/1999 | Takeuchi et al. |
| 5,997,147 A | 12/1999 | Tatoian |
| 6,001,057 A | 12/1999 | Bongiovanni |
| 6,011,701 A | 1/2000 | Kopp et al. |

(56) References Cited

U.S. PATENT DOCUMENTS

| | | |
|---|---|---|
| 6,012,693 A | 1/2000 | Voeller et al. |
| 6,015,120 A | 1/2000 | Sweere et al. |
| 6,019,332 A | 2/2000 | Sweere et al. |
| 6,027,247 A | 2/2000 | Tachi et al. |
| 6,061,104 A | 5/2000 | Evanicky et al. |
| 6,064,373 A | 5/2000 | Ditzik |
| 6,065,732 A | 5/2000 | Cho |
| 6,073,285 A | 6/2000 | Ambach et al. |
| 6,089,518 A | 7/2000 | Nilsson |
| 6,102,476 A | 8/2000 | May et al. |
| 6,102,855 A | 8/2000 | Kehr et al. |
| 6,104,443 A | 8/2000 | Adcock et al. |
| 6,112,182 A | 8/2000 | Akers et al. |
| 6,125,350 A | 9/2000 | Dirbas |
| 6,134,103 A | 10/2000 | Ghanma |
| 6,143,181 A | 11/2000 | Falkvall et al. |
| 6,144,848 A | 11/2000 | Walsh et al. |
| 6,146,523 A | 11/2000 | Kenley et al. |
| 6,150,942 A | 11/2000 | O'Brien |
| 6,154,139 A | 11/2000 | Heller |
| RE36,978 E | 12/2000 | Moscovitch |
| 6,155,603 A | 12/2000 | Fox |
| 6,155,975 A | 12/2000 | Urich et al. |
| 6,168,250 B1 | 1/2001 | Rogov |
| 6,170,102 B1 | 1/2001 | Kreuzer |
| 6,175,779 B1 | 1/2001 | Barrett |
| 6,175,977 B1 | 1/2001 | Schumacher et al. |
| 6,176,456 B1 | 1/2001 | Wisniewski |
| 6,179,260 B1 | 1/2001 | Ohanian |
| 6,183,417 B1 | 2/2001 | Geheb et al. |
| 6,189,842 B1 | 2/2001 | Bergeron Gull et al. |
| 6,202,360 B1 | 3/2001 | Rattner et al. |
| 6,202,923 B1 | 3/2001 | Boyer et al. |
| 6,205,601 B1 | 3/2001 | Nessmann et al. |
| 6,219,587 B1 | 4/2001 | Ahlin et al. |
| 6,234,172 B1 | 5/2001 | Ausbourne et al. |
| 6,246,573 B1 | 6/2001 | Khan et al. |
| 6,260,761 B1 | 7/2001 | Peoples, Jr. |
| 6,352,504 B1 | 3/2002 | Ise et al. |
| 6,493,568 B1 | 12/2002 | Bell et al. |
| 6,510,049 B2 | 1/2003 | Rosen |
| 6,611,979 B2 | 9/2003 | Welling et al. |
| 6,616,606 B1 | 9/2003 | Petersen et al. |
| 6,658,680 B2 | 12/2003 | Osborne et al. |
| 6,825,763 B2 | 11/2004 | Ulrich et al. |
| 6,838,992 B2 | 1/2005 | Tenarvitz |
| 6,972,683 B2 | 12/2005 | Lestienne et al. |
| 7,032,522 B2 | 4/2006 | George et al. |
| 7,053,831 B2 | 5/2006 | Dempsey et al. |
| 7,099,895 B2 | 8/2006 | Dempsey |
| 7,154,397 B2 | 12/2006 | Zerhusen et al. |
| 7,237,287 B2 | 7/2007 | Weismiller et al. |
| 7,403,111 B2 | 7/2008 | Tessier et al. |
| 7,444,704 B2 | 11/2008 | Phillips et al. |
| 7,450,024 B2 | 11/2008 | Wildman et al. |
| 7,567,794 B2 | 7/2009 | Dempsey |
| 7,679,520 B2 | 3/2010 | Zerhusen et al. |
| 7,715,387 B2 | 5/2010 | Schuman |
| 7,734,476 B2 | 6/2010 | Wildman et al. |
| 7,907,053 B2 | 3/2011 | Wildman et al. |
| 7,911,349 B2 | 3/2011 | Zerhusen et al. |
| 7,962,981 B2 | 6/2011 | Lemire et al. |
| 7,979,169 B2 | 7/2011 | Rawls-Meehan |
| 8,018,584 B1 | 9/2011 | Amir |
| 8,082,160 B2 | 12/2011 | Collins, Jr. et al. |
| 8,139,945 B1 | 3/2012 | Amir et al. |
| 8,169,304 B2 | 5/2012 | Schuman, Sr. et al. |
| 8,310,364 B2 | 11/2012 | Derks et al. |
| 8,334,779 B2 | 12/2012 | Zerhusen et al. |
| 8,384,526 B2 | 2/2013 | Schuman, Sr. et al. |
| 8,392,747 B2 | 3/2013 | Ferguson et al. |
| 8,572,778 B2 | 11/2013 | Newkirk et al. |
| 8,618,918 B2 | 12/2013 | Tallent et al. |
| 10,290,071 B2 | 5/2019 | Heil et al. |
| 10,474,808 B2 | 11/2019 | Huster |
| 2002/0014951 A1* | 2/2002 | Kramer ............... G16H 10/60 340/286.07 |
| 2002/0038392 A1 | 3/2002 | De La Huerga |
| 2002/0044059 A1 | 4/2002 | Reeder et al. |
| 2002/0053086 A1 | 5/2002 | Vanderpohl, III et al. |
| 2002/0152211 A1 | 10/2002 | Jam |
| 2002/0196150 A1 | 12/2002 | Wildman |
| 2003/0052787 A1 | 3/2003 | Zerhusen et al. |
| 2003/0093503 A1 | 5/2003 | Yamaki et al. |
| 2005/0246416 A1 | 11/2005 | Blomquist |
| 2006/0049936 A1 | 3/2006 | Collins, Jr. et al. |
| 2006/0180054 A1 | 8/2006 | George et al. |
| 2007/0120689 A1 | 5/2007 | Zerhusen et al. |
| 2007/0136098 A1 | 6/2007 | Smythe et al. |
| 2008/0235872 A1 | 10/2008 | Newkirk et al. |
| 2009/0112630 A1 | 4/2009 | Collins, Jr. et al. |
| 2009/0212925 A1 | 8/2009 | Schuman, Sr. et al. |
| 2009/0212956 A1 | 8/2009 | Schuman et al. |
| 2009/0300507 A1 | 12/2009 | Raghavan et al. |
| 2010/0154124 A1 | 6/2010 | Zerhusen et al. |
| 2010/0212087 A1* | 8/2010 | Leib .................... A61G 12/00 5/81.1 R |
| 2010/0234718 A1* | 9/2010 | Sampath ............... G16H 40/67 600/407 |
| 2011/0105854 A1* | 5/2011 | Kiani .................... G16Z 99/00 600/300 |
| 2011/0240448 A1 | 10/2011 | Springer et al. |
| 2011/0247139 A1 | 10/2011 | Tallent et al. |
| 2012/0089419 A1 | 4/2012 | Huster et al. |
| 2012/0173257 A1 | 7/2012 | Preiss et al. |
| 2012/0179289 A1 | 7/2012 | Moy et al. |
| 2013/0018672 A1 | 1/2013 | Wong et al. |
| 2013/0219615 A1 | 8/2013 | Eklof et al. |
| 2013/0283529 A1 | 10/2013 | Hayes et al. |
| 2013/0311766 A1 | 11/2013 | Lortz et al. |
| 2013/0312066 A1 | 11/2013 | Suarez et al. |
| 2013/0314866 A1 | 11/2013 | Millman |
| 2013/0339039 A1 | 12/2013 | Román et al. |
| 2014/0080413 A1 | 3/2014 | Hayes et al. |
| 2014/0123390 A1 | 5/2014 | Meyer et al. |
| 2014/0124274 A1 | 5/2014 | Zerhusen et al. |
| 2014/0182059 A1 | 7/2014 | Jonsson |
| 2014/0259414 A1* | 9/2014 | Hayes ................ A61B 5/7275 600/595 |
| 2014/0297327 A1 | 10/2014 | Heil et al. |
| 2015/0033295 A1 | 1/2015 | Huster |
| 2016/0213537 A1 | 7/2016 | Hayes et al. |

FOREIGN PATENT DOCUMENTS

| | | |
|---|---|---|
| GB | 2218149 A | 11/1989 |
| GB | 2333391 A | 7/1999 |
| WO | 94/13198 A1 | 6/1994 |
| WO | 98/02107 A1 | 1/1998 |
| WO | 98/29775 A1 | 7/1998 |
| WO | 99/52487 A1 | 10/1999 |
| WO | 01/57610 A2 | 8/2001 |
| WO | 2013/097930 A1 | 7/2013 |
| WO | 2013/140613 A1 | 9/2013 |

OTHER PUBLICATIONS

Cohen, Martin H., et al., "Patient handling and movement assessments: a white paper." Dallax, TX: The Facility Guidelines Institute (2010): 1-144, available at https://www.mnhospitals.org/Portals/0/Documents/ptsafety/lift/FGI_PHAMAwhitepaper_042710.pdf.

Studer, A., Passaro, T., and Bauer, L., Don't Bump, Shake on It: The Exploitation of a Popular Accelerometer-Based Smart Phone Exchange and Its Secure Replacement, article, Dec. 5-9, 2011, ACSAC '11, Orlando, Florida, USA.

* cited by examiner

UNIVERSAL INTERFACE OPERABLE WITH MULTIPLE PATIENT SUPPORT APPARATUSES

CROSS REFERENCE TO RELATED APPLICATIONS

The present application is a continuation of U.S. application Ser. No. 14/501,380, filed Sep. 30, 2014, now U.S. Pat. No. 10,474,808, which is a continuation-in-part application of U.S. application Ser. No. 14/223,355, filed Mar. 24, 2014, now U.S. Pat. No. 10,290,071, which claims the benefit, under 35 U.S.C. § 119(e) of U.S. Provisional Patent Application Nos. 61/806,556 and 61/806,771 which were both filed on Mar. 29, 2013, and each of which are hereby incorporated by reference herein in their entirety.

BACKGROUND

The present disclosure relates systems in which hospital beds run third party application software on computer hardware of the hospital bed. More particularly, the third party software is downloaded to the hospital bed from another computer device of a network of a healthcare facility.

The present disclosure is also related to care systems that distribute computing power between multiple components of the system. More specifically, the present disclosure is related to a system which permits a mobile computing device to act as a user interface for a patient support apparatus and transfer computing requirements for the patient support apparatus to a remote server to reduce the processing load on the patient support apparatus.

The present disclosure further relates to medical equipment, such as hospital beds, and particularly to a universal caregiver interface that is used to control multiple pieces of medical equipment. More particularly, the present disclosure relates to wall mounted and portable universal caregiver interfaces.

As patient support systems, such as hospital beds with therapy mattresses become more complex, the computing power required to operate the systems expands. Certain aspects of the computing power are associated with critical or safety related functions of the patient support system. Other aspects are non-critical, such that completion of the processing will not affect the safety of the patient supported on the patient support system. All aspects of the software of a patient support system are subject to stringent safety standards, even those that are non-critical. This results in resources being consumed to qualify non-critical software as meeting safety related standards.

Furthermore, as the functionality of the patient support systems expands, the concern with interference by non-qualified individuals with the delivery of therapy by the patient support systems grows. A balance between the ease of use for a caregiver and the inability of a non-caregiver to access therapy data is an important part of the development of user interfaces for patient support systems and patient support surfaces.

In the healthcare setting, caregivers come into contact with a wide variety of patient care devices such as hospital beds, patient lifts, intravenous (IV) pumps, vital signs monitors, therapy delivery devices, and so forth. To control each of these patient care devices, caregivers must touch or otherwise contact user inputs such as buttons, knobs, and touch screens, of each individual patient care device. Caregivers also touch other types of equipment found in a patient room environment such as window blinds, thermostats, and light switches.

Each time a caregiver contacts a surface in a patient room, there is a risk that the caregiver becomes contaminated with germs or bacteria and there is a risk that the caregiver contaminates the surface with germs or bacteria. Accordingly, it would be beneficial to reduce the number of surfaces that a caregiver needs to contact in order to control multiple pieces of equipment in a patient room environment.

Various pieces of patient care devices generate a wide variety of patient data and device data. Typically, when a caregiver is in a patient room, the caregiver will have to move from device to device to view the desired data. Accordingly, it would be beneficial to have data from various patient care devices viewable on a single display screen.

Some procedures within a patient room involve the use of multiple patient care devices or room environment devices. For example, during patient transfer from a hospital bed to a stretcher, a patient lift is sometimes used. As another example, when a patient is discharged from a patient room, a scale system of the bed should be zeroed, the window blinds should be opened, and a patient lift should be moved back into a storage cabinet. Accordingly, it would be beneficial for caregivers to be able to control multiple pieces of equipment simultaneously.

SUMMARY

The present application discloses one or more of the features recited in the appended claims and/or the following features which, alone or in any combination, may comprise patentable subject matter:

According to a first aspect of the present disclosure, a system comprises a server, a beacon identifying a physical location, a patient support system associated with the physical location and in electrical communication with the server, and a mobile computing device. The mobile computing device includes a first communication system for communicating with the server. The mobile computing device includes a second communication system capable of detecting the beacon. The mobile computing device is operable to transmit a signal to the server indicative of the beacon and a control command indicative of a desired change in state of the patient support system. The server processes the signal and transmits the control command to the patient support system through the electrical connection.

In some embodiments, the first and second communications systems comprise wireless communication systems.

In some embodiments, the server is in electrical communication with the patient support system through physical communications connection.

In some embodiments, the first communication system is a 3G communication system.

In some embodiments, the second communications system is a Bluetooth® communications system.

In some embodiments, the electrical connection is an Ethernet connection.

In some embodiments, the mobile computing device controls functions which are not accessible from a user interface on the patient support system.

According to another aspect of the present disclosure, a system comprises a server, a patient support system, and a mobile computing device. The patient support system includes first communications circuitry in electrical communication with the server and second communications circuitry. The mobile computing device includes first communication circuitry for communicating with the server and second communication circuitry capable of communicating with the second communications circuitry of the patient support system. The mobile computing device is operable to receive a signal from the patient support system, establish a one-to-one communications link with the second communications circuitry of the patient support system, and transmit to the server a signal indicative of the ongoing communications with the patient support system. The mobile computing device is also operable to transmit information from the patient support system to the remote server. The server processes the signal and transmits the information from the patient support system to a hospital information system.

In some embodiments, the mobile computing device may include operational circuitry used by a caregiver to enter patient related information.

In some embodiments, the mobile computing device associates the patient related information with the information from the patient support system and transmits the associated data to the remote server.

In some embodiments, the remote server transmits instructions intended for the patient support system to the mobile computing device.

In some embodiments, the mobile computing device is configured such that a user may optionally allow the instructions from the server intended for the patient support system to be transmitted by the mobile computing device to the patient support system.

In some embodiments, the patient support system may include a user interface and the remote server is operable to enable the mobile computing device to access functionality of the patient support system that is not accessible from the user interface, the functionality accessible being dependent on the authority level of the mobile computing device.

According yet another aspect of the present disclosure, a system comprises a server, and a first patient support system. The first patient support system includes first communications circuitry in communication with the server and a controller, the controller operable to control functionality of the patient support system. The controller of the first patient support system is operable to communicate data to the server. The data communicated to the server is processed by the server to reduce the processing load of the controller of the first patient support system. Upon completion of the processing of the data, the server is operable to return the results of the processed data to the controller of the first patient support system.

In some embodiments, the system further comprises a second patient support system including first communications circuitry in communication with the server and a controller. The controller of the second patient support system is operable to control functionality of the patient support system. The controller of the second patient support system is operable to communicate data to the server. The data communicated to the server by the controller of the second patient support system is processed by the server to reduce the processing load of the controller of the second patient support system. Upon completion of the processing of the data, the server is operable to return the results of the processed data to the controller of the second patient support system.

In some embodiments, the first and second patient support systems each further include second communications circuitry. In some embodiments, the system further comprises a mobile computing device including communications circuitry operable to communicate with the second communications circuitry of each of the first and second patient support systems. The mobile computing device may include operations circuitry which permits the mobile computing device to be paired with only one of the first and second patient support systems.

In some embodiments, the controllers of the first and second patient support systems transfer data to the server which is associated with non-critical functionality of the patient support systems to reduce the processing load on the controllers.

In some embodiments, mobile computing device acts as a user interface for the patient support system with which the mobile computing device is paired.

In some embodiments, the controller of the first patient support system transfer data to the server which is associated with non-critical functionality of the patient support systems to reduce the processing load on the controller.

In some embodiments, the first patient support system may further include second communications circuitry. The system may further comprise a mobile computing device including communications circuitry operable to communicate with the second communications circuitry of the first patient support system. The mobile computing device may include operations circuitry which permits the mobile computing device to be paired with the first patient support systems. The mobile computing device acts as a user interface for the first patient support system when the first patient support system and the mobile computing device are paired.

According to this disclosure a system for use in a healthcare facility having a plurality of patient rooms may include a plurality of patient care devices located in a first patient room of the plurality of patient rooms. An application server may be located remotely from the first patient room. The application server may have stored therein application software that may be associated with each patient care device of the plurality of patient care devices. At least one universal caregiver interface may be situated in the first patient room and may be in communication with the application server. The at least one universal caregiver interface may receive application software from the application server. The at least one universal caregiver interface may then be usable to control the operation of each of the plurality of patient care devices in accordance with the application software.

In some embodiments, the at least one caregiver interface may include a first universal caregiver interface that may be mounted to a wall of the patient room. It is contemplated by this disclosure that, in some instances, after the application software for the plurality of caregiver devices in the first patient room is received by the first universal caregiver interface, the first universal caregiver interface may be operable by a caregiver to communicate control commands wirelessly to at least one of the plurality of patient care devices without involving the application server. Alternatively or additionally, after the application software for the plurality of caregiver devices in the first patient room is received by the first universal caregiver interface, the first universal caregiver interface may be operable by a caregiver to communicate control commands to at least one of the plurality of patient care devices via the application server.

In some embodiments, the system may include an electronic medical records (EMR) computer device located remotely from the patient room. The first universal caregiver interface may serve as a hub to collect data from each of the plurality of patient care devices in the room. The first universal caregiver interface may send the data to the EMR computer device for storage in an electronic medical record of a patient located in the patient room.

In some embodiments, the system may further include a computer on wheels (COW) that may be transportable to the first patient room. The first universal caregiver interface may send data wirelessly to the COW in response to the COW being transported to the first patient room and after a communication link is established between the COW and the first universal caregiver interface. Alternatively or additionally, the system may include a wireless communication device carried by a caregiver. The first universal caregiver interface may send at least some of the data wirelessly to the wireless communication device in response to the wireless communication device being transported to the first patient room and after a communication link is established between the wireless communication device and the first universal caregiver interface.

According to this disclosure, the at least one universal caregiver interface may comprise a tablet computer that may be carried by a caregiver. In some embodiments, both a tablet computer and a wall-mounted universal caregiver interface may be used. The system may have a receiver located in the first patient room. The receiver may be in communication with the application server. The second tablet computer may receive the application software from the application server in response to the tablet computer being transported into the first room by the caregiver and communicating a wireless signal to the receiver. The receiver may be included as part of a wireless access point, for example. The application server may send the application software to the tablet computer via the wireless access point in such embodiments.

In some embodiments, at least one of the plurality of patient care devices may include a hospital bed and the at least one universal caregiver interface, be it a tablet computer or a wall-mounted universal caregiver interface, may be usable to control the hospital bed. Alternatively or additionally, the application server may send application software to the hospital bed for use in controlling at least one patient care device other than the hospital bed via a user interface of the hospital bed. In some embodiments, a second of the plurality of patient care devices may include a lift and the at least one universal caregiver interfaces each may be usable to control the lift. According to some embodiments contemplated by this disclosure, the at least one universal caregiver interface may include an input for bed exit coordination in which the lift may be moved to a use position, a bed exit alarm of the hospital bed may be suppressed, and a patient exit from the hospital bed may be charted to an electronic medical records (EMR) computer device located remotely from the patient room.

In some embodiments, the system may further include at least one motorized window blind, a thermostat to control room temperature, and at least one room light. The at least one universal caregiver interface may receive environment controls application software from the application server. The at least one universal caregiver interface may be usable to control the operation of each of the at least one motorized window blind, the thermostat, and the at least one room light in accordance with the environment controls application software.

Alternatively or additionally, the at least one universal caregiver interface may include an input that may be selected to place the patient room in a night mode in which the at least one motorized window blind may be closed, the thermostat may be adjusted, the at least one room light may be turned off, and a bed exit system of the hospital bed may be enabled. Further alternatively or additionally, the at least one universal caregiver interface may include a room ready input that may be selected to set a bed scale of the hospital bed to zero, to open the at least one motorized window blind, and to cancel any room notifications associated with the patient room.

According to this disclosure, the plurality of patient care devices may include an intravenous (IV) pump which may be usable to deliver medicine to a patient. The at least one universal caregiver interface may be usable to initiate the delivery of the medicine to the patient by operation of the IV pump. In such embodiments, the at least one universal caregiver interface may send a message to an electronic medical records (EMR) computer device located remotely from the patient room to indicate at least one of a time at which medicine delivery to the patient was started and the medicine delivery to the patient. The at least one universal caregiver interface may receive an order pertaining to the delivery of the medicine to the patient.

According to some embodiments of this disclosure, the at least one universal caregiver interface may include a user interface of a first patient care device of the plurality of patient care devices. For example, the first patient care device may comprise a hospital bed. Alternatively or additionally, the at least one universal caregiver interface may comprise a smart phone. Further alternatively or additionally, the at least one universal caregiver interface may comprise an in-room computer.

According to an aspect of this disclosure, the at least one universal caregiver interface may include a wireless mobile device carried by a caregiver and default patient data displayed on a display screen of the wireless mobile device may vary automatically depending upon the caregiver's location within the healthcare facility. For example, the default patient data may include heart rate data and respiration data when the caregiver is located in the patient room with the patient. The default patient data may include a previous radiological image or a current radiological image when the caregiver is in a radiology portion of the healthcare facility with the patient. The default patient data may include laboratory test results when the caregiver is in a laboratory testing portion of the healthcare facility with the patient. In some embodiments, the default data displayed on the display of the wireless mobile device may be filtered based on the caregiver's role.

According to another aspect of this disclosure, the default patient data displayed on a display screen of the wireless mobile device may vary automatically depending upon a patient schedule. For example, the default patient data may include heart rate data and respiration data when the patient is scheduled to be in the patient room. The default patient data may include at least one of a previous radiological image and a current radiological image when the patient is scheduled to be in a radiology portion of the healthcare facility. The default patient data may include laboratory test results when the patient is scheduled to be in a laboratory testing portion of the healthcare facility. The default data displayed on the display of the wireless mobile device may be filtered based on the caregiver's role.

In some embodiments, the system may include a patient interface that is used by a patient to communicate with the at least one universal caregiver interface. The patient interface may also be used to control at least one patient care device of the plurality of patient care devices. The patient interface, therefore, may receive application software from the server.

According to still a further aspect of this disclosure, a system may include a remote computer device and a patient bed in communication with the remote computer device. The patient bed may have circuitry operable by a user to obtain at least one software application from the remote computer device. The system further may have an authentication software module that may verify that the at least one software application is authorized for use on the patient bed. The at least one software module may be unusable on the patient bed until verification has occurred.

In some embodiments, the authentication software module may be stored in the circuitry of the patient bed. Alternatively or additionally, the authentication software module may be stored in the remote computer device. In some embodiments, the authentication software module may use serial number approval to verify that the at least one software application is authorized for use on the patient bed. Alternatively or additionally, the authentication software module may use secure certificate exchange to verify that the at least one software application is authorized for use on the patient bed. Further alternatively or additionally, the authentication software module may use a Dynamic Link Library (DLL) to verify that the at least one software application is authorized for use on the patient bed.

It is contemplated by this disclosure that the circuitry of the patient bed may prioritize core bed functionality over functionality of the at least one software application. In this regard, the circuitry of the patient bed may use a publish/subscribe engine to prioritize messages. The at least one software application may include an electronic medical records (EMR) software application, for example.

The system may further include at least one patient care device that may be located in a patient room with the patient bed. The remote computer device may have stored therein device application software associated with the at least one patient care device. The device application software may be downloaded to the circuitry of the patient bed. In some embodiments, the patient bed has a user interface that may be used to provide inputs to the device application software for control of the at least one patient care device.

The system may further have a patient interface that may be used by a patient to communicate with the remote computer device. The patient interface may also be used to control the patient bed in some embodiments.

The circuitry of the patient bed may have a user interface that may be used to initiate downloading of the at least one software application to the circuitry of the patient bed. In some embodiments, the circuitry of the patient bed may have a Universal Serial Bus (USB) to Ethernet interface for direct access to a network. In some embodiments, the circuitry of the patient bed may have at least one pre-authenticated software module stored therein for at least one of communication and control of a device other than the patient bed.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
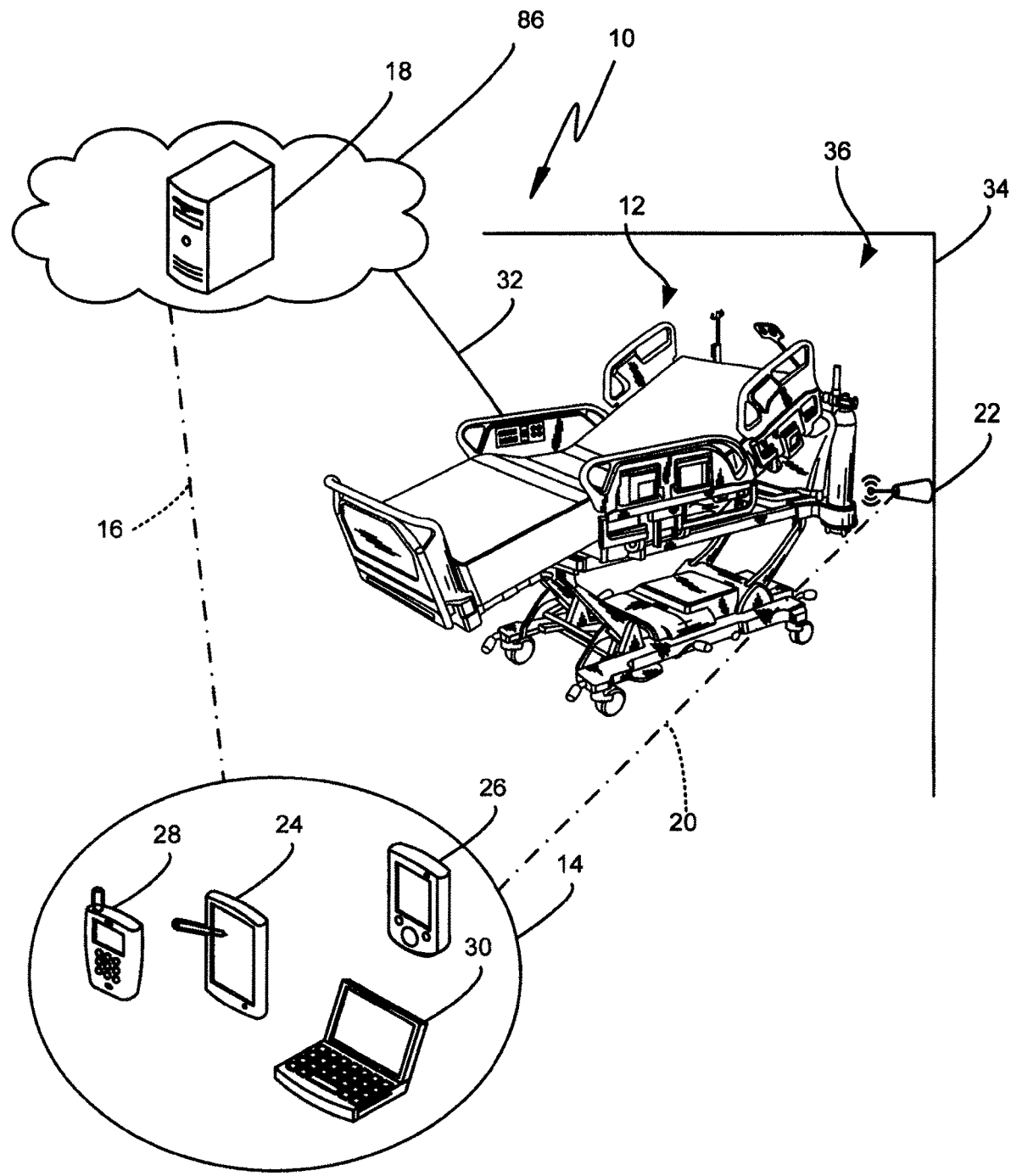
FIG. 1 is a diagrammatic view of a care system that includes a remote server in communication with a mobile computing device and a patient support system.
Figure 2:
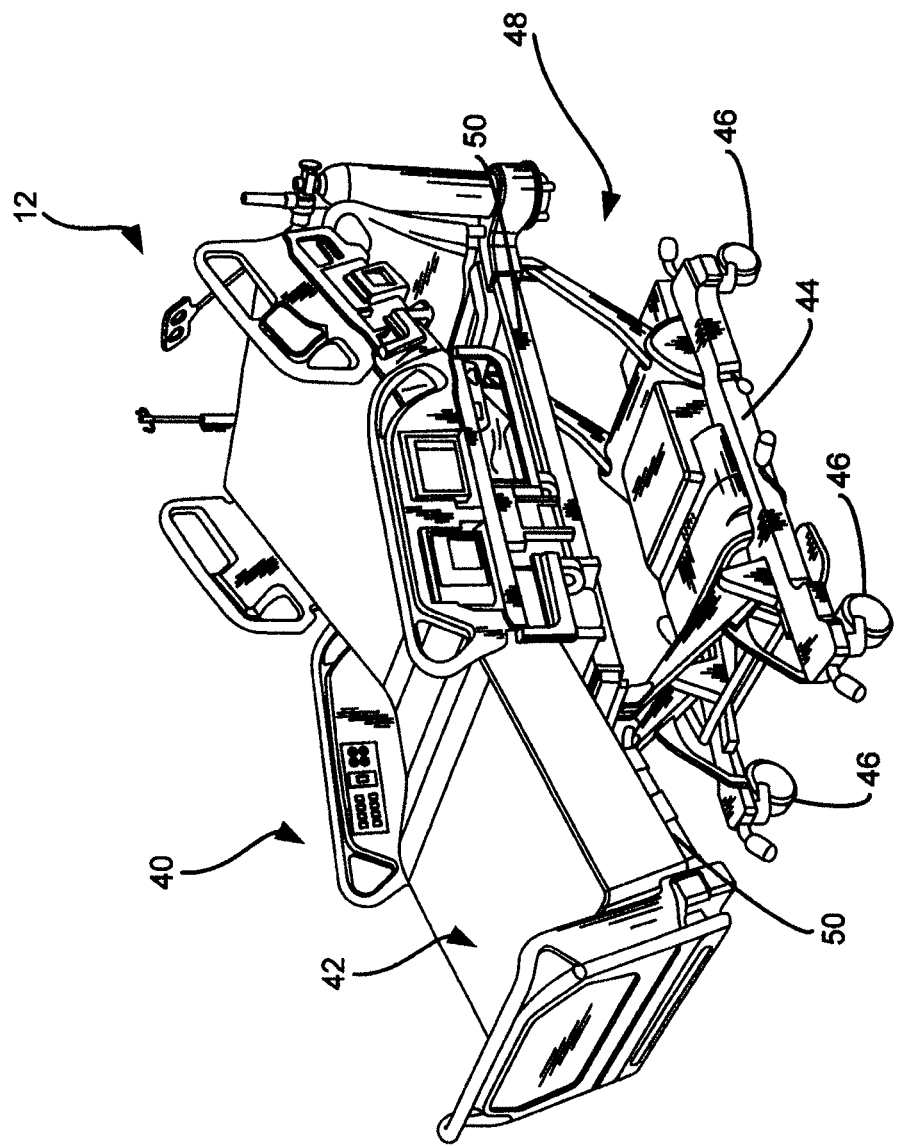
FIG. 2 is a perspective view of the patient support system of FIG. 1 including a patient support surface supported on a patient support apparatus.

A care system 10 illustratively includes a patient support system 12, a mobile computing device 14, and a remote server 18 as shown in FIG. 1. The patient support system (sometimes called a patient bed or hospital bed) 12 is a medical device configured to support and provide therapies to a patient in a care setting. As shown in FIG. 2, the patient support system 12 includes a patient support apparatus 40 and a patient support surface 42. The patient support surface 42 includes structures, such as inflatable bladders, that act as therapy devices 102. In some embodiments, a patient support system 12 may include only one or the other of a patient support apparatus 40 and patient support surface 42. The mobile computing device 14 is illustratively used to by a caregiver for multiple functions including controlling the operation of the patient support system. The mobile computing device 14 in the illustrative embodiment is configured to communicate through a first wireless communication link 16 with the remote server 18 and a second wireless communication link 20 with a beacon 22 to identify the location of the patient support system 12 to thereby associate the patient support system 12 with the mobile computing device 14.

Figure 3:
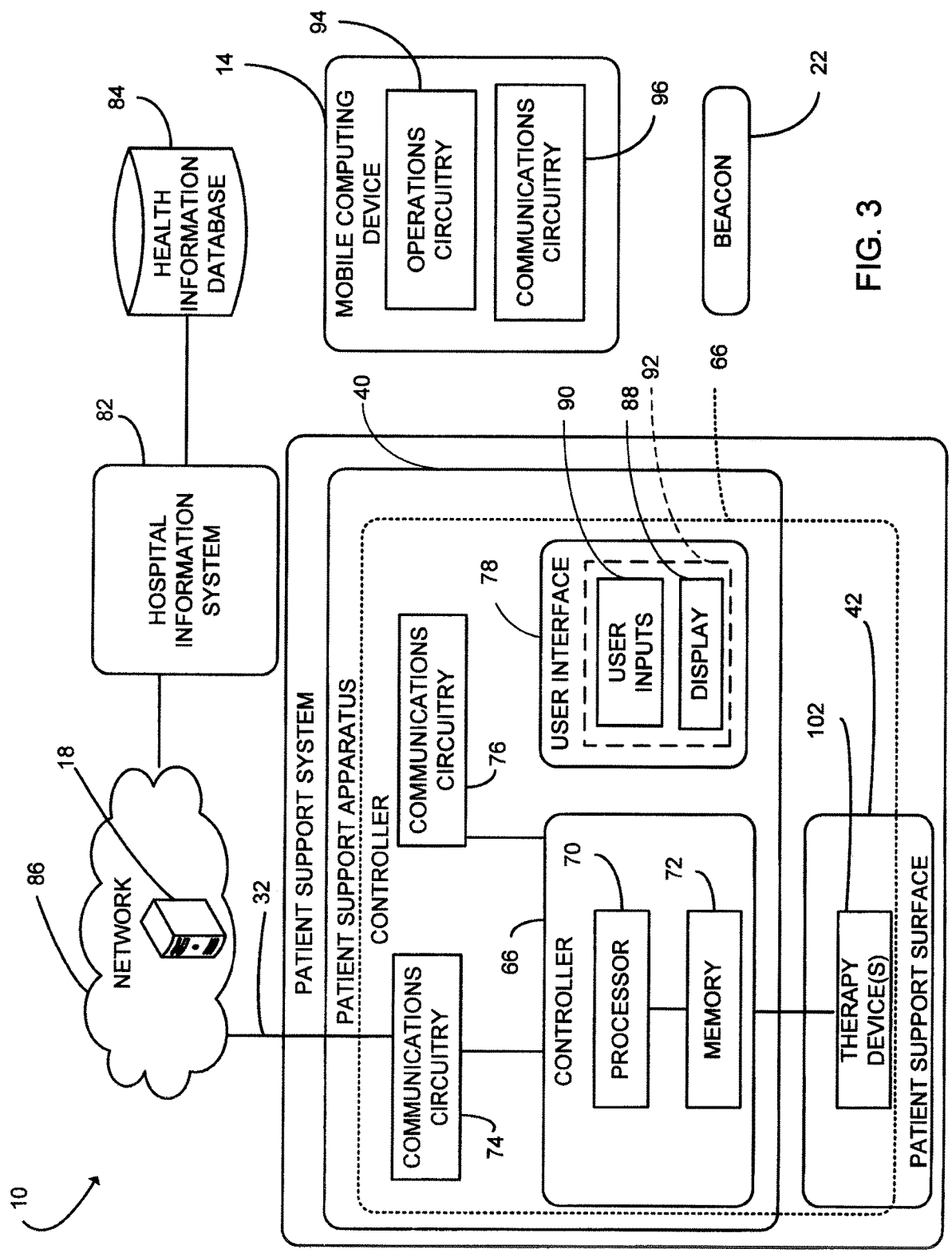
FIG. 3 is a block diagram of the care system of FIG. 1.

Referring to FIG. 3, the remote server 18 is part of a network 86 with a hospital information system 82 which is in communication with a health information database 84. The remote server 18 includes software that allows the remote server 18 to manage communications with either the patient support system 12 or the mobile computing device 14.

Referring again to FIG. 1, the mobile computing device 14 may be embodied as any one of a tablet computer 24, a personal digital assistant 26, a smart phone 28, or a laptop computer 30. The mobile computing device 14 is operable to "pair" with the beacon 22 such that information related to the beacon 22 is available to the mobile computing device 14 while the two are paired. The beacon 22 is associated with a specific configuration of patient support system 12 such that the beacon 22 provides sufficient information to the mobile computing device 14 to allow the mobile computing device 14 to identify the specific patient support system 12 to remote server 18. The patient support system 12 is coupled to the remote server 18 by a communication link 32 which is illustratively a hardwired connection. In other embodiments, the patient support system 12 may include a wireless transceiver that permits the patient support system 12 to communicate to the remote server 18 through a wireless communication link.

In the illustrative embodiment, the beacon 22 and mobile computing device 14 each include Bluetooth® technology such that the wireless communication link 20 is a Bluetooth® connection. It should be understood that the mobile computing device 14 is configured such that the user must explicitly accept a pairing of the mobile computing device with a specific beacon 22. In the illustrative embodiment, a user must accept the beacon 22 so that the user is responsible for identifying the appropriate beacon 22 when coming into contact with a particular patient support system 12. This is especially important when the mobile computing device 14 is used in a facility with a number of different patient support systems 12 so that the mobile computing device 14 is only paired with a single particular patient support system 12 at any given time.

The care system 10 is operable to permit a user to remotely control functionality on the patient support system 12 from the mobile computing device 14 through the remote server 18 and to gather information from the patient support system 12 through the remote server 18. In addition, the remote server 18 is operable to transmit data to the mobile computing device 14, which allows the mobile computing device 14 to provide a user interface for the patient support system 12 to a user, such as a caregiver, for example. Because a user, such as a caregiver, may utilize a single mobile computing device 14 throughout all of their responsibilities, having the ability to control the patient support system 12 without physically interacting with the patient support system 12 provides several advantages to the user. For example, if the user is charting patient information and implementing medical orders utilizing the mobile computing device 14, the user may change an operational characteristic of the patient support system 12 to implement the medical order without having to interact with the structure of the patient support system 12. Furthermore, the user may gather historical operational data regarding the operation of the patient support system 12 and update a patient's electronic medical record to show that a specific therapy was provided by the patient support system 12 simply by having the information transferred from the patient support system 12 to the remote server 18 which thereby permits the information to be communicated with the mobile computing device 14. This reduces the need for a caregiver to rekey or otherwise enter data which is available from the patient support system 12.

Still further, the mobile computing device 14 may also transmit data and/or software to the remote server 18 which then controls the transfer of the software and/or data to the patient support system 12. As shown in FIG. 1, the beacon 22 is independent from the patient support system 12 and is coupled to a wall 34 of a room 36 in which the patient support system 12 is positioned. In the illustrative embodiment, the particular patient support system 12 is associated with a location identified by the beacon 22 at the remote server 18 so that the remote server 18 maintains that association. In other embodiments, the beacon 22 may be coupled directly to the patient support system 12, thereby eliminating the need for the association of the specific location of the patient support system 12 within the remote server 18.

Figure 6:
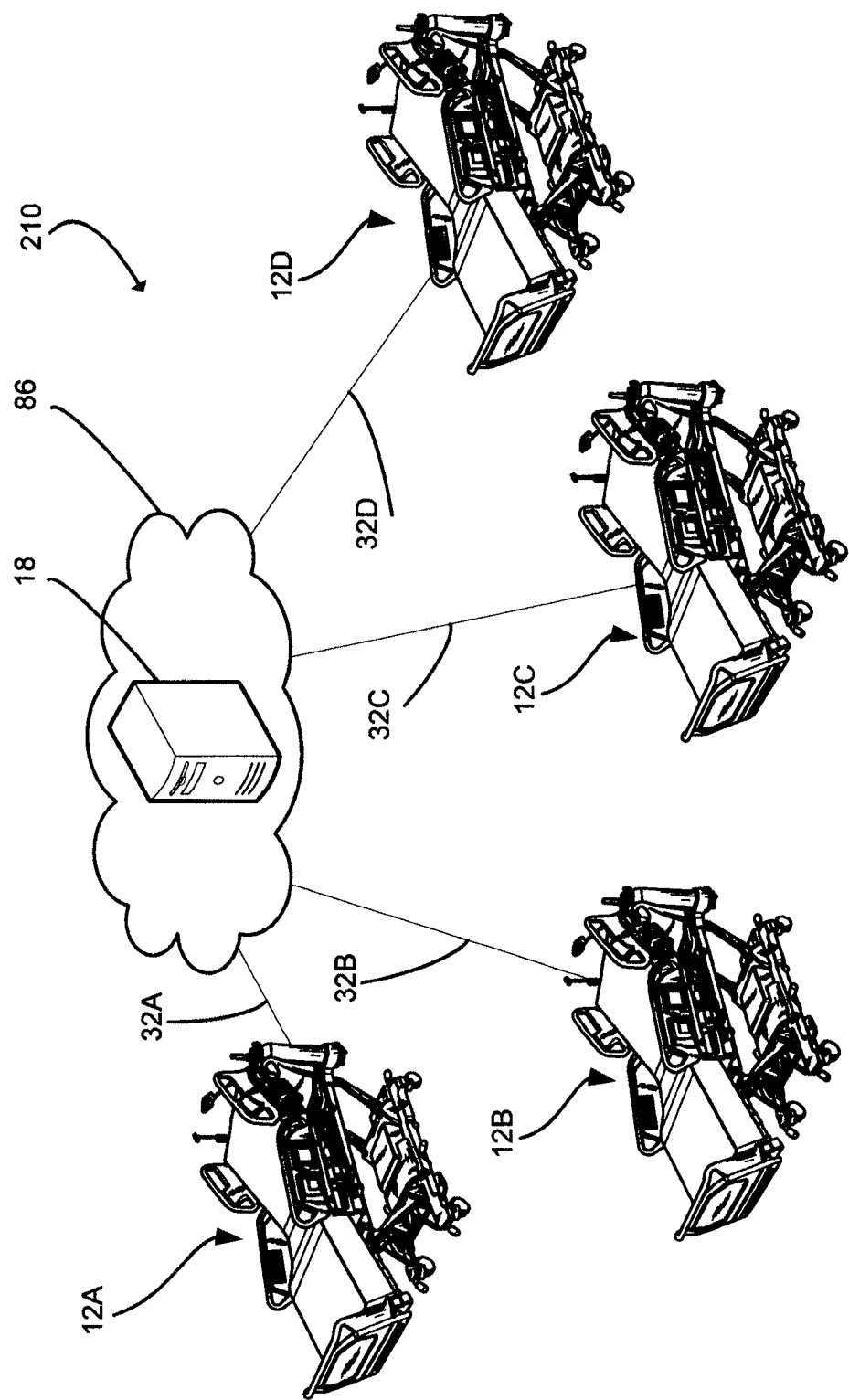
FIG. 6 is a diagrammatic representation of a single remote server serving as a central computing resource for a number of different patient support systems.

In some embodiments, the remote server 18 is used as a remote processor for handling at least some processing that may be necessary at the patient support system 12. For example, the remote server 18 may perform operations that are not critical to the operation of the patient support system 12 to thereby reduce the complexity of the software on the patient support system 12. For example, the remote server 18 may include processing software that processes voice data to convert the voice data to machine useable data and return the machine useable data to the patient support system 12. This reduces the computing power required of the patient support system 12 and allows a single higher speed computer device, the remote server 12, to perform complex algorithms centrally. The remote server 12 may also be more easily updated with software improvements. This reduces the opportunity for non-essential/non-critical tasks, such as converting voice to data, from consuming vital processing resources on the patient support system 12. Thus, a single remote server 18 may provide computing resources for multiple patient support systems 12A, 12B, 12C, and 12D as suggested by FIG. 6. The patient support apparatuses 12A, 12B, 12C, and 12D are each connected to the network 86 via respect communications links 32A, 32B, 32C, and 32D.

Referring now to FIG. 2, the patient support system 12 is illustratively embodied as a patient support apparatus 40 (sometimes referred to as a bed frame) which supports a patient support surface 42 (sometimes referred to as a mattress) with the patient support system 12 being operable to move a patient supported on the patient support surface 42 to a number of positions and to provide therapy through the patient support surface 42 to the patient. In the illustrative embodiment of FIG. 2, the patient support apparatus 40 includes a lower frame 44 supported on a number of casters 46 which permit the patient support apparatus 40 to be moved over a floor.

The patient support apparatus 40 further includes a lift system 48 and an upper frame 50 supported on the lift system 48 so that the upper frame 50 moves relative to the lower frame 44 when the lift system 48 is operated. The patient support apparatus 40 further includes a deck 52 that includes multiple sections movable relative to the upper frame 50. The patient support apparatus 40 includes a number of barriers including a headboard 54, a footboard 56, a left head rail 58, a right head rail 60, a left foot rail 62, and a right foot rail 64.

The patient support surface 42 includes a number of inflatable bladders (not shown) which are operable to provide various therapies to a patient supported on the patient support surface. The patient support surface 42 may include all of the functionality disclosed in U.S. patent application Ser. No. 13/828,186, filed Mar. 14, 2013, and entitled "PATIENT SUPPORT SYSTEMS AND METHODS OF USE," which is hereby incorporated by reference in it's entirety for the patient support surface functionality disclosed therein.

A control system 66 for the patient support system 12 is shown in FIG. 3 and includes a controller 68 which includes a processor 70 and a memory device 72. Operation of the patient support system 12 is controlled by the processor 70 which executes instructions stored in the memory device 72 to effect operation of the patient support system 12. It should be understood that the control system 66 may include multiple controllers with specific functionality distributed to separate controllers having specific functions. The multiple controllers may each communicate with one another via a network, with one or more of the controllers in communication with the remote server 18.

In the illustrative embodiment, the controller 68 controls the functionality of both the patient support apparatus 40 and the patient support surface 42. In other embodiments, the patient support surface 42 may be a mattress replacement system which includes a separate control system and operates independently of the patient support apparatus 40. In those embodiments where the patient support surface 42 has an independent control system, both the patient support apparatus 40 and the patient support surface 42 may be associated with a particular location such that the beacon 22 identifies both the patient support apparatus 40 and the patient support surface 42 to be controlled by the mobile computing device 14. The control system 66 further includes communication circuitry 74 that is operable to communicate with the network 86. Additional communications circuitry 76 facilitates wireless communication with the mobile computing device 14. The control system further includes a user interface 78 that includes a display 88 and a plurality of user inputs 90. In some embodiments, the user interface 78 may include a touch screen 92 which is shown in phantom in FIG. 3 to indicate that the display 88 and user inputs 90 may be part of the touch screen 92.

The mobile computing device 14 includes operations circuitry 94 and communications circuitry 96. It should be understood that in some embodiments, the communications circuitry 96 may include a first portion that is operable to communicate via a first wireless protocol and a second portion operable to communicate via a second wireless protocol. Wireless protocols that may be used include Bluetooth®, IEEE 802.11n (Wi-Fi), IEEE 802.16e (WiMAX), mobile communications technologies such as 3G or 4G technology, or other wireless In still other embodiments, the communications circuitry 96 may include circuitry that allows the mobile computing device 14 to communicate via a hardwired connection using an IEEE 802.3 connection, an RS-232 compliant connection, an RS-483 compliant connection, or other protocols known in the art.

Figure 4:
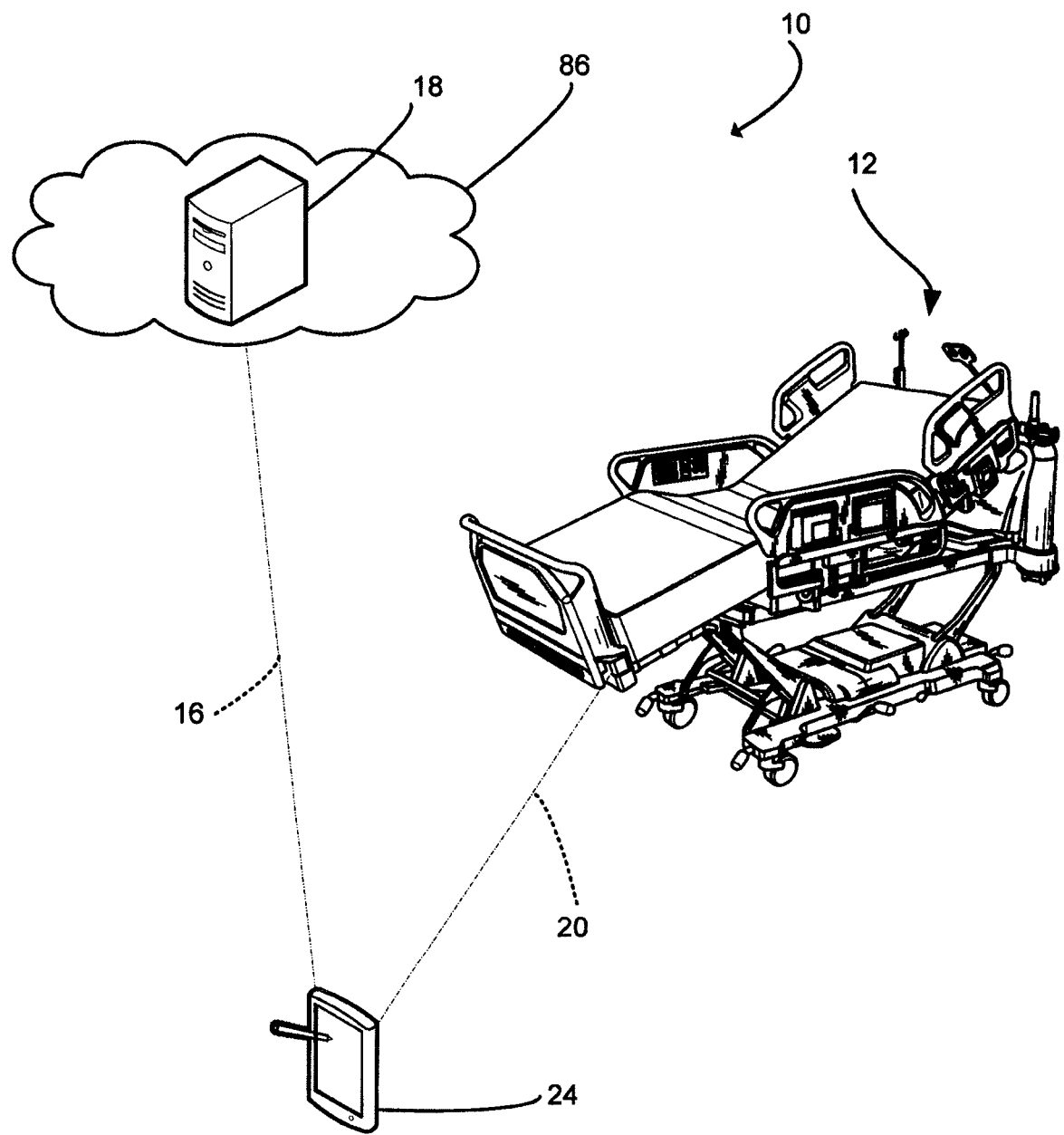
FIG. 4 is a diagrammatic view of another embodiment of a care system configured such that a mobile computing device communicates with a patient support system and a remote server.

In another embodiment of a care system 110, shown in FIG. 4, the beacon 22 is omitted and a mobile computing device 14 embodied as a tablet computer 24 is paired with the patient support system 12 through a wireless communication link 112, illustratively utilizing a Bluetooth protocol. In addition, the tablet computer 24 maintains communication through the wireless communication link 16 with the remote server 18. In the embodiment of care system 110, the identity of the particular patient support system 12 is transferred to the tablet computer 24 over the wireless communication link 112. Because the specific identity of the patient support system 12 is known by the tablet computer 24, the tablet computer 24 can access the appropriate information from the remote server 18.

Utilizing the embodiment of FIG. 4, a user may control operational characteristics of the patient support system 12 and share specific information with the remote server 18. In addition, it is contemplated that additional functionality beyond that typically available from a user interface 80 of the patient support system 12 may be made available to the tablet computer 24 via the remote server 18. For example, the tablet computer 24 may be associated with expanded functionality that may include the ability to perform maintenance and diagnostic operations on the patient support system 12. Furthermore, functionality may normally be reserved for use by a caregiver, such as a nurse, for example, may be available only through the tablet computer 24 or other similar mobile computing device 14. This reduces the risk that a non-authorized individual may access functionality of the patient support system 12 by completely eliminating access to that functionality through the typical user interface 80. In this way, the control of access to functionality of the patient support system 12 may be controlled by controlling access to a particular mobile computing device 14 which is authorized for the restricted functionality.

In the illustrative embodiment of care system 110, the remote server 18 may also be operable to push updates to software for the patient support system 12 to the tablet computer 24 such that a user may review and authorize the update to the patient support system 12 via the tablet computer 24.

Pairing of the tablet computer 24 and patient support system 12 in the illustrative embodiment is accomplished in a manner similar to that used when pairing Bluetooth® devices or establishing a Wi-Fi connection. Typically, the tablet computer will recognize a new patient support system 12 within the range of communication of the tablet computer 24. Upon detection of the signal from the new patient support system 12, the tablet computer 24 will prompt the user to accept pairing with the particular patient support system 12. In the illustrative embodiment, only one patient support system 12 may be actively paired with a particular mobile computing device 14, such as the tablet computer 24. One-to-one pairing of this type prevents an inadvertent or unexpected operational condition in which a particular tablet computer 24 or other mobile computing device 14 is simultaneously communicating with two different patient support systems 12. In other embodiments, other methods of pairing the devices may be implemented such as, for example, physically contacting the mobile computing device with the patient support system 12 similar to the Bump method of sharing data between mobile devices as implemented by Bump Technologies, LLC of Mountain View, California. Another approach is the Shot technology described in "Don't Bump, Shake on It: The Exploitation of a Popular Accelerometer-Based Smart Phone Exchange and Its Secure Replacement," by Studer et al., available at http://www.ece.cmu.edu/~lbauer/papers/2011/acsac2011-pairing.pdf. Other approaches my include a proprietary or dedicated radio-frequency identification, near-field communication connection, pairing switches, or other pairing methods known in the art to confirm that two devices should be paired to permit communication therebetween.

In the care system 110, the tablet computer 24 functions as both a user interface for the patient support system 12 and a data entry device which allows a caregiver to inputs patient related data to a patient medical record stored at the remote server 18 or a memory location accessible by the remote server 18. This permits the caregiver to collect data regarding the operation of the patient support system 12, combine that data with patient medical information, and transfer all of the information together to update the patient electronic medical record. For example, the caregiver charts a patient's vital signs and other information as a part of normal rounding as well as uploads the most recent history of therapy provided by the patient support system 12 since the last update. This allows the patient's electronic medical records include both patient vitals data as well as a firm historical record of the therapy is delivered to the patient by the patient support system 12.

Figure 5:
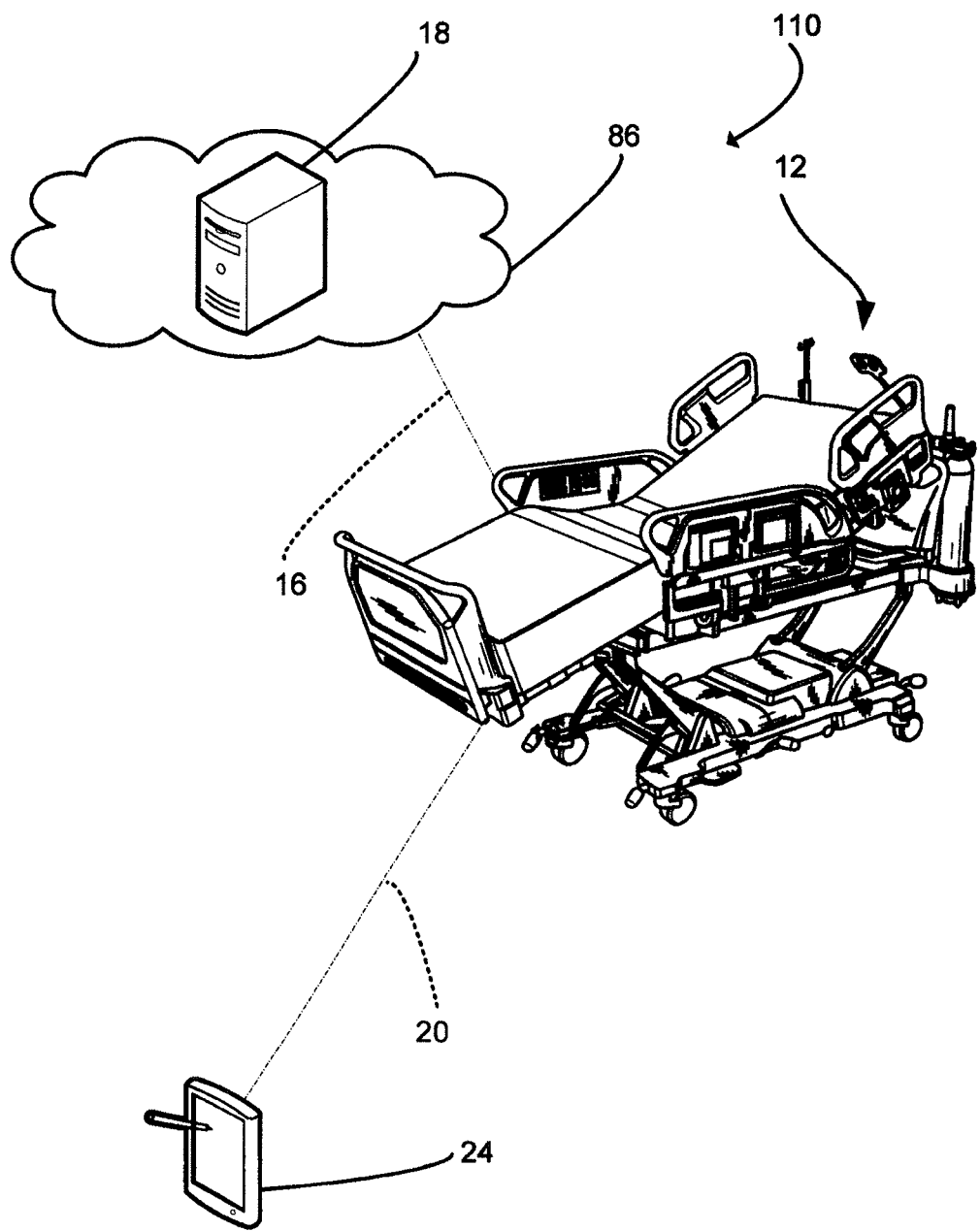
FIG. 5 is a diagrammatic view of yet another embodiment of a care system, the care system of FIG. 5 configured such that a mobile computing device communicates with a patient support system and the patient support system communicates with a remote server.

In yet another embodiment of a patient care system 210, shown in FIG. 5, the mobile computing device 14 is illustratively embodied as a laptop computer 30. The laptop computer 30 communicates with the patient support system 12 through a wireless communication link 212, illustratively embodied as a Wi-Fi connection. The patient support system 12 includes a Wi-Fi access point and is connected to the remote server 18 through the communication link 32 as discussed above with regard to the care system 10. In the patient care system 210, a user, such as a caregiver, may control operation of functional aspects of the patient support system 12 from the laptop computer 30 as well as enter information into an electronic medical record that is transferred through the Wi-Fi connection to the patient support system 12. Upon receiving the transfer of electronic medical record data, the patient support system 12 transfers the electronic medical record data along with operational performance data of the patient support system 12 together to the remote server 18 to be stored at the remote server or at a memory location accessible by the remote server 18.

Another aspect of the configuration of care system 210 is that a mobile computing device 14 such as the laptop computer 30 may be used by an occupant of the patient support system 12 to access remote data through the patient support system 12. For example, an occupant may access information they have stored in the "cloud" for various applications thereby allowing them to download music, movies, books, calendars, or other information of interest to the occupant. In this way, the mobile computing device 14 functions as a client to the server 18 with the patient support system 12 functioning as an access point for the client to access information in the cloud or at the remote server 18.

The various configurations of care systems 10, 110, and 210 have several common advantages. The use of the mobile computing device 14 to access and operate the patient support system 12 obviates the need for a separate graphical user interface on each patient support system 12. Under this paradigm, their only need be a user interface available for each potential user, where the user leverages the mobile computing devices that exist in the care environment to access and operate a patient support system 12. Continual access to the remote server 18 by the mobile computing device 14 permits the latest software associated with a particular patient support system 12 to be available via the remote server 18. Furthermore, the care systems 10, 110, and 210 facilitate a relatively simple Association of patient support system 12 operational statistics with other information regarding the patient so that the combined information may be stored together in an electronic medical record.

Figure 7:
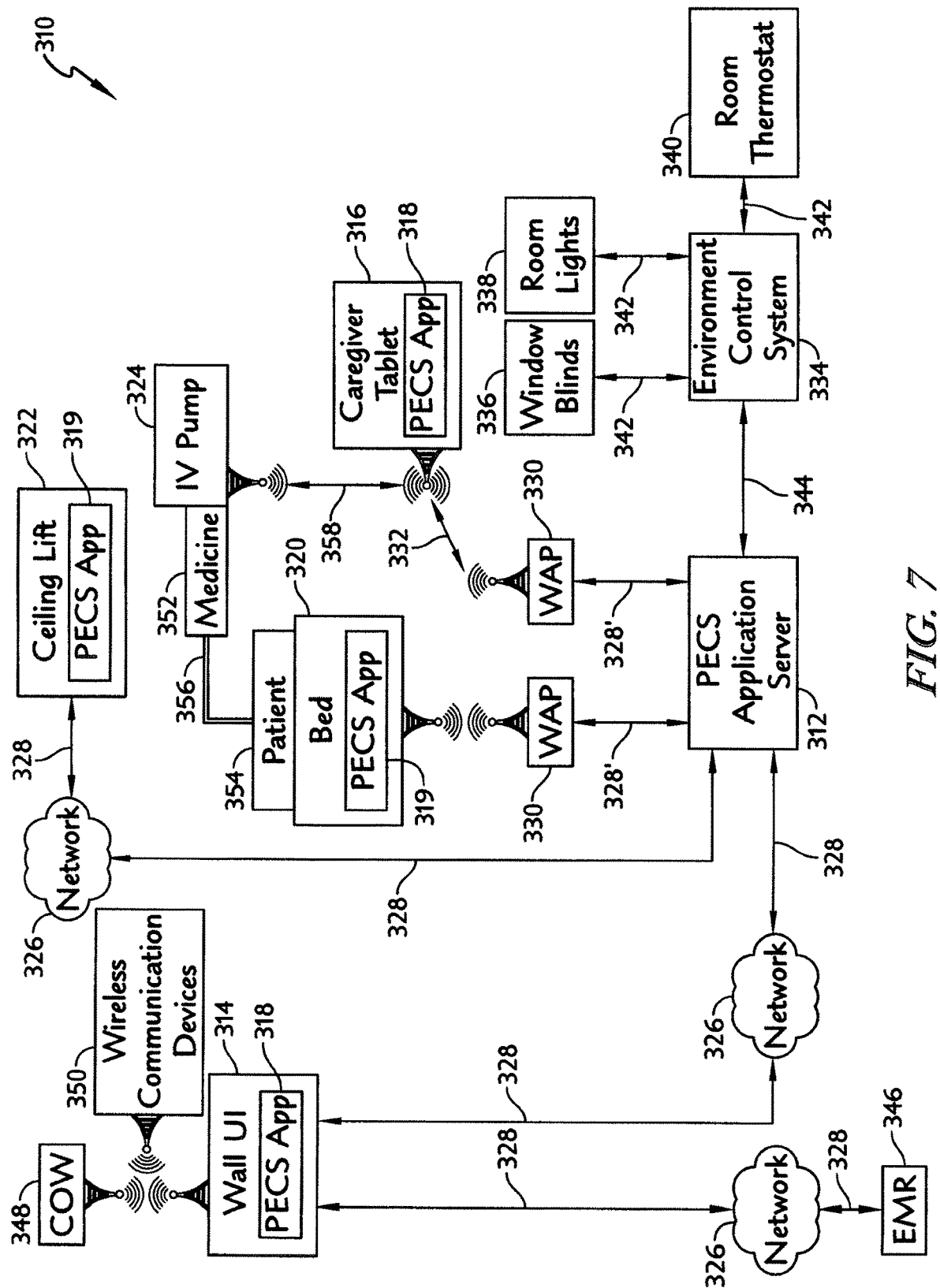
FIG. 7 is a block diagram of a healthcare information technology system in which universal caregiver interfaces are used to control a plurality of patient care devices based on application software received by the universal caregiver interfaces from an application server, one of the universal caregiver interfaces being a wall-mounted user interface, and another of the universal caregiver interfaces being a tablet computer.

A system 310 for use in a healthcare facility includes a patient environment control system (PECS) application server 312 which provides application software 318 to a wall-mounted universal caregiver interface 314 and to a wireless universal caregiver interface 316 as shown diagrammatically in FIG. 7. In the illustrative example of FIG. 7, interface 314 is labeled as "Wall UI" and interface 316 is labeled as "Caregiver Tablet." The application software 318 sent to interfaces 314, 316 by server 312 is configured to control various patient care devices that are located within a particular room of the healthcare facility. Thus, the various patient care devices located in the patient room are controlled by either universal caregiver interface 314, universal caregiver interface 316, or both. In other embodiments of system 310, one or the other of universal caregiver interfaces 314, 316 is omitted.

In the illustrative example, the patient care devices located in the patient room include a bed 320, a ceiling lift 322, and an intravenous pump 324 as shown diagrammatically in FIG. 7. However, it is contemplated by this disclosure that other types of patient care devices, such as vital signs monitors including blood pressure monitors, pulse oximeters, electrocardiographs (EKG's), electroencephalographs (EEG's), just to name a few, and therapy devices such as passive motion devices, respiratory therapy devices, and wound therapy devices, just to name a few, may be located within the patient room and controlled by one or both of universal caregiver interfaces 314, 316 based on application software 318 received by caregiver interfaces 314, 316 from server 312.

Server 312, therefore, stores in its memory application software 318 for a wide variety of devices and equipment that, at any given instance, may be located in a patient room. Such patient care devices and equipment may be manufactured by a wide variety of equipment manufacturers. Accordingly, coordination with a number of equipment manufacturers may be required in order to obtain the application software for a respective patient care device. It will be appreciated, therefore, that the software code and routines for the application software 318 for any particular piece of equipment is beyond the scope of this disclosure. Suffice it to say, having a server download or upload application software 318 to a remote computer device, such as interfaces 314, 316, is known in the art, regardless of what algorithms are contained in the actual software programming. Furthermore, if server 312 does not have application software for certain devices located in a patient room, then interfaces 314, 316 are not usable to control those particular devices and the individual user interfaces for those particular devices need to be used.

In the illustrative example, wall interface 314 is communicatively coupled to server 312 via network infrastructure 326. Network infrastructure 326 is sometimes referred to herein simply as network 326. Double headed arrows 328 indicate the communication of data, including device control commands, from interface 314 to server 312 via network 326 and the communication of application software 318 from server 312 to interface 314. In FIG. 7, network 326 is shown diagrammatically and, in conjunctions with arrows 328, is intended to represent the components that interconnect server 312 with other computer devices of system 310 as well as representing the other computer devices themselves. Such components include, for example, wires, cables, routers, gateways, repeaters, additional servers, etc. Networks 326, of course, vary from healthcare facility to healthcare facility and thus, the construction and configuration of such networks 326 is at the discretion of the information technology personnel of any given healthcare facility.

System 310 also includes wireless access points (WAP's) 330 which are in bidirectional communication with server 312 as indicated diagrammatically in FIG. 7 with double headed arrows 328'. In some embodiments, network infrastructure 326 is included in the communication link 328' between server 312 and WAP's 330. However, in the illustrative example of FIG. 7, network 326 is omitted from communications link 328'. In any event, server 312 communicates wirelessly via one of WAP's 330 with universal caregiver interface 316 as indicated diagrammatically in FIG. 7 with double headed arrow 332.

In order for server 312 to determine which application software 318 to provide to interfaces 314, 316, server 312 maintains a database of which patient care devices, such as devices 320, 322, 324 are located in a particular patient room, and server 312 also determines which interfaces 314, 316 are also present in the same room as the devices. This disclosure contemplates several ways in which this is done. For example, interfaces 314 are wall mounted in particular rooms and thus, an association between an interface identification (ID) of each interface 314 and a particular room ID is made within the database of server 312. This interface-to-room association does not change as long as each interface 314 remains installed in each associated room. In the illustrative example, ceiling lift 322 is installed in a particular patient room and thus a lift-to-room association is made in the database of server 312 in a similar manner. In the case of interface 314 and ceiling lift 322, it will be appreciated that the communication links 328 to network 326 and server 312 are hardwired connections in some embodiments.

Server 312 also maintains, within its database, a WAP-to-room association which, as its name implies, associates a WAP ID of each WAP 330 with a room ID. Devices within a patient room having wireless communication capability with one or more WAP's 330 send their respective device ID's to the WAP 330, which then forwards the device ID with the WAP ID to server 312 which, in turn, makes the device-to-room association. In the illustrative example of FIG. 7, bed 320 is shown to be in wireless communication with one of WAP's 330 and thus, bed 320 sends its bed ID to WAP 330 which, in turn, sends the bed ID and its respective WAP ID to server 312. Based on this information, server 312 then stores in its database the bed-to-room association. The presence of universal caregiver interface 316 in the patient room is determined by server 312 in a similar way. That is, interface 316 sends its ID to one or more of the WAP's 330 in a particular room, as indicated diagrammatically with double headed arrow 332 in FIG. 1, and then the respective WAP 330 sends its ID and the interface ID to server 312 which, in turn, stores in its database the interface-to-room association.

In some embodiments, badges or tags worn by caregivers communicate with a WAP 330 or similar locating and tracking receiver in order for server 312 or another server of network 326 to track the whereabouts of caregivers within a healthcare facility. In such embodiments, a database of server 312 or another server of network 326 stores the ID's of the universal caregiver interfaces 316 assigned to the various caregivers. Thus, when it is determined that a caregiver is in a particular room of a healthcare facility based on a wireless signal that is transmitted from the associated badge or tag via a WAP 330 located in the room and that includes a badge or tag ID along with a WAP ID, server 312 responds by sending to the universal caregiver interface 316 assigned to the caregiver sensed to be in the room, the application software 318 for each of the patient care devices located in the room, to the extent the application software 318 is among the software stored in server 312 or stored in a storage device associated with server 312. In some embodiments, locating and tracking tags are attached to mobile patient care devices, such as bed 320 and IV pump 324, for use in tracking the whereabouts of such devices in a similar manner.

In FIG. 7, two WAP's 330 are shown as being in the same patient room to illustrate that the wireless communication technologies or protocols of the WAP's 330 are different from each other in some embodiments. For example, it is contemplated by this disclosure that one of WAP's 330 communicates using a radio frequency (RF) or Wi-Fi technology, such as those according to the Bluetooth (e.g. IEEE 802.15.1 et seq.) or Zigbee (e.g. IEEE 802.15.4) communication protocols, whereas the other WAP 330 communicates using an infrared (IR), ultrasound, or ultra wide band (UWB) communication technology. Accordingly, WAP's 330 are intended to represent all types of devices having wireless communication capability which provide a communication portal to a network 326.

In the illustrative example, therefore, one or more of WAP's 330 cooperate with server 312 to provide the healthcare facility with a real time locating system (RTLS) to track the whereabouts of equipment, such as devices 320, 324, 326 and interfaces 314, 316. In some embodiments, the RTLS tracks the whereabouts of caregivers as discussed above. In other embodiments, a separate RTLS is provided and includes its own server that communicates equipment tracking information (e.g., device-to-room, interface-to-room, patient-to-room, caregiver-to-room, etc.) to server 312. Such RTLS systems are available from companies such as Hill-Rom Company, Inc. of Batesville, Indiana; Centrak, Inc. of Newtown, Pennsylvania; and Radianse, Inc. of Andover, Massachusetts. Additional details of locating and tracking systems, such as an RTLS, can be found in U.S. Pat. Nos. 8,310,364; 8,139,945; 8,082,160; 8,018,584; 7,907,053; 7,734,476; 7,715,387; 7,450,024; 7,567,794; 7,403,111; 7,099,895; 7,053,831; 6,972,683; 6,838,992; 6,825,763; 6,154,139 and 5,455,851; each of which is hereby expressly incorporated by reference herein in its entirety to the extent not inconsistent with the present disclosure which shall control as to any inconsistencies.

After server 312 determines which patient care devices, such as devices 320, 324, 326 and which interfaces 314, 316 are located in a particular patient room, server 312 sends application software 318 to each interface 314, 316 present in the room so that interfaces 314, 316 are usable by caregivers to provide inputs to control each device 320, 324, 326. In some embodiments, server 312 also sends application software 319 to the patient care devices to facilitate the ability of interfaces 314, 316 to control the patient care devices. In the illustrative example of FIG. 7, application software 319 is provided to bed 320 and to lift 322 by server 312. In some embodiments, application software 318 includes validation information that enables the patient care devices to confirm that received device command messages are being sent by authorized interfaces 314, 316.

The application software 318 sent to one or more of interfaces 314, 316, when executed by the microprocessors or microcontrollers of interfaces 314, 316, cause graphical user interface screens to be displayed on the respective universal caregiver interfaces 314, 316. In some embodiments, user interfaces 314, 316 display a list or menu of the patient care devices which are controllable by the interfaces 314, 316 based on the software applications 319 received from server 312. The caregiver selects the device the caregiver wishes to control and the associated graphical user interface screens appear on the display screen of the user interface 314, 316. Thus, each interface 314, 316 comprises a touch screen display that is used by the caregiver to control functions of the patient care devices in the room.

The interfaces 314, 316 display the same user interface screens that are displayable on graphical user interfaces (GUI's) of the associated patient care devices in some embodiments. For example, some hospital beds have GUI's that are used to control features and functions of the bed. Examples of the types of user interface screens shown on the GUI's of beds can be found in the following, each of which is hereby expressly incorporated by reference herein in its entirety to the extent not inconsistent with this disclosure which shall control as to any inconsistencies: U.S. Pat. No. 8,334,779; U.S. Patent Application Publication Nos. 2012/0089419 A1 and 2008/0235872 A1; and U.S. application Ser. No. 13/798,359, filed Mar. 13, 2013, and titled "Patient Support Systems and Methods of Use."

Alternatively or additionally, interfaces 314, 316 display other types of user inputs such as knobs, buttons, switches, sliders, and the like that are provided on control panels or housings, for example, of the associated patient care devices. For example, some hospital beds have control panels with buttons or switches, such as membrane switches, that are used to raise and lower an upper frame relative to a base frame and that are used to articulate a mattress support deck to a number of positions. Interfaces 314, 316 are controlled by the application software 318 to emulate such other types of user inputs and control panels in some embodiments. By touching and/or dragging motions over switches, buttons, knobs and sliders shown on the touch screens of interfaces 314, 316, for example, caregivers are able to control the patient care devices just as if manipulating the manual user input on the patient care device itself.

Universal caregiver interfaces 314, 316 also are operable to display any information that is able to be displayed as outputs on screens or other types of visual indicators such as alert lights, including light emitting diodes (LED's), of the associated patient care devices. For example, some beds 320 display information such as patient weight and a head angle of a head section of the mattress support deck. Such information is available for display on interfaces 314, 316 by navigating to the appropriate screens on interfaces 314, 316 just as the caregiver would do on the patient care device itself In some embodiments, the output information shown on the patient care device is shown on interface 314, 316 during the entire duration that interfaces 314, 316 are being used to control the respective patient care device.

While most patient care devices, such as beds 320, lifts 322, and pumps 324 have their own user inputs, this disclosure also contemplates patient care devices that have no user inputs thereon, or that have minimal user inputs (e.g., an on/off switch only) thereon. In such embodiments, universal caregiver interfaces 314, 316 are the primary means of controlling such patient care devices once server 312 provides the application software 318 to interfaces 314, 316. This is beneficial for devices that should not be operated by anyone other than a knowledgeable caregiver. Accordingly, when an appropriate caregiver is not present in the room, patients and visitors, for example, are unable to operate these types of patient care devices because there are no control inputs on the devices that are accessible for the patients or visitors to manipulate. In this regard, it will be appreciated that wall-mounted interface 314 is locked out from use until an authorized caregiver is sensed to be present in the room so that unauthorized people are prevented from using interface 314 when no authorized caregiver is present in the room. In some embodiments, patient care devices without user inputs include a port or connector for a service technician to directly couple a laptop computer or tablet computer, for example, to operate the patient care device during service, inspection, or maintenance.

In the illustrative example, system 310 includes an environment control system 334 which sends signals to control the operation of room environmental devices such as one or more window blinds 336, one or more room lights 338, and a room thermostat 340 as shown diagrammatically in FIG. 7. Thus, control system 334 includes a computer device in some embodiments which communicates control signals to blinds 336, lights 338, and thermostat 340 as indicated diagrammatically with double headed arrows 342. In some embodiments, a position of window blinds 336 is adjusted using a motor and a suitable linkage mechanism as is known in the art. Thus, system 334 signals the motor of blinds 336 to open or close the blinds or to move the blinds to any number of intermediate positions between the opened and closed positions. System 334 controls room lights 338 by turning the lights on or off, such as by use of a relay or by dimming the lights, such as by use of a voltage controller or potentiometer to limit the amount of current or voltage delivered to the lights 338. System 334 controls thermostat 340 by sending target temperature data to thermostat 340.

According to this disclosure, universal caregiver interfaces 314, 316 are able to control blinds 336, lights 338, and thermostat 340 based on application software 318 received from server 312. Thus, once interfaces 314, 316 are loaded with the proper software 318, caregivers enter user input commands on one of interfaces 314, 316 which, in turn, communicates the user input command via network 326 and/or WAP 330 to server 312 which, then, forwards the user input command to control system 334 which ultimately controls blinds 336, lights 338 or thermostat 340 in accordance with the user input command entered at interface 314 or interface 316. Thus, server 312 is communicatively linked to control system 334 as indicated diagrammatically in FIG. 7 with doubled headed arrow 344.

According to an aspect of this disclosure, wall-mounted interface 314 serves as a master communication and data capture device or hub in the patient room. That is, patient data and device data is sent to interface 314, either via server 312 and network 326 or via direct wireless communication to interface 314, from the various patient care devices in the room, such as one or more of illustrative devices 320, 322, 324. Interface 314 then communicates some or all of the patient and device data via network 326 and communication links 328 to an Electronic Medical Records (EMR) computer device 346 for storage in the associated patient's electronic medical record.

Alternatively or additionally, some or all of the patient data and device data is also communicated by interface 314 to a computer on wheels (COW) 348 and other wireless communication devices 350 having wireless data communication capability. The COW 348 and wireless communication devices 350 are able to store and display the patient data and device data. In some embodiments, the data is displayed automatically and in other embodiments, the data is displayed after a caregiver requests to see the information via user inputs on COW 348 or devices 350. Wireless communication devices 350 include, for example, cellular telephones, smart phones (e.g., iPhone available from Apple Inc. of Cupertino, California), wireless telephone handsets, personal data assistants (PDA's), and tablet computers (e.g., iPad available from Apple Inc. of Cupertino, California).

In some embodiments, interface 314 sends patient data and/or device data from one of the patient care devices in the patient room to another patient care device in the room.

Thus, decisions concerning the operation of features and functions of one patient care device are made based on patient data and/or device data originating at another patient care device. To give one example, if interface 314 receives information indicating that lift 322 is being deployed for patient transfer, interface 314 communicates that information to bed 320 and then bed 320 responds by operating its pneumatic control system to inflate mattress bladders to a max inflate or firm condition to facilitate the patient transfer. In some embodiments, interface 316 serves as a data transfer intermediary between patient care devices in the patient room.

According to this disclosure, data or information regarding the use of interfaces 314, 316 to control various patient care devices is also logged or stored in EMR computer device 346 and/or in server 312. For example, in the illustrative example, IV pump 324 is of the type that is capable of delivering medicine 352 through an IV line 356 to a patient 354 supported on bed 324. In one scenario, a caregiver provides user inputs on interface 316 to signal pump 324 to start the delivery of the medicine 352 to the patient 354 as indicated diagrammatically in FIG. 7 with double headed arrow 358. Pump 324 operates to deliver the medicine 352 to the patient 356 and signals interface 316 when the medicine delivery is complete. Interface 316 sends a medicine delivery start and end time to the EMR computer device 346 via WAP 330, server 312 and network 326 along with the associated communication links 328, 328'. In some embodiments, a physician's order to deliver the medicine to the patient is entered into system 310 at a computer device (e.g., COW 348 or EMR computer device 346) and the order is communicated to one or both of interfaces 314, 316 so that the caregiver sees the order and carries it out. Thus, the physician's order appears in a pop-up window which is displayed by interfaces 314, 316 substantially immediately upon receipt in some embodiments.

Further according to this disclosure, interfaces 314, 316 display one or more icons or buttons or other types of graphical user inputs that are selected by a caregiver to simultaneously control multiple patient care devices, such as bed 320, lift 322, and IV pump 324, and/or environmental equipment, such as window blinds 336, room lights 338, and thermostat 340. For example, in some embodiments, a night mode input is shown on one or both of interfaces 314, 316 and is selected by a caregiver to place the patient room in a night mode in which the at least one motorized window blind 336 is closed, the thermostat 340 is adjusted either up or down at the discretion of the system programmer, the at least one room light 338 is turned off, and a bed exit system of the hospital bed 320 is enabled. As another example, a room ready input is shown on one or both of interfaces 314, 316 and is selected by a caregiver to set a bed scale of the hospital bed 320 to zero, to open the at least one motorized window blind 336, and to cancel any room notifications associated with the patient room. The room notifications may include, for example, recurring rounding reminders or periodic reminders regarding turning a patient that are tracked in a nurse call system. As yet another example, an input for bed exit coordination is shown on one or both of interfaces 314, 316 and is selected by a caregiver to move lift 322 to a use position, to suppress a bed exit alarm of the hospital bed 320, and to chart a patient exit from the hospital bed 320 to the EMR computer device 346 which is located remotely from the patient room.

It is within the scope of this disclosure for wall-mounted interface 314 to also serve as a graphical room station (GRS), sometimes referred to as a graphical audio station (GAS), of a nurse call system. The other components of such a nurse call system are not shown in FIG. 7 so as not to clutter up the figure. However, details of a suitable nurse call system in which interface 314 is included, in some embodiments, is found in U.S. Pat. Nos. 8,392,747; 8,384,526; and 8,169,304 and in U.S. Patent Application Publication No. 2009/0212956 A1, each of which is hereby expressly incorporated by reference herein in its entirety to the extent not inconsistent with this disclosure which shall control as to any inconsistencies.

Figure 8:
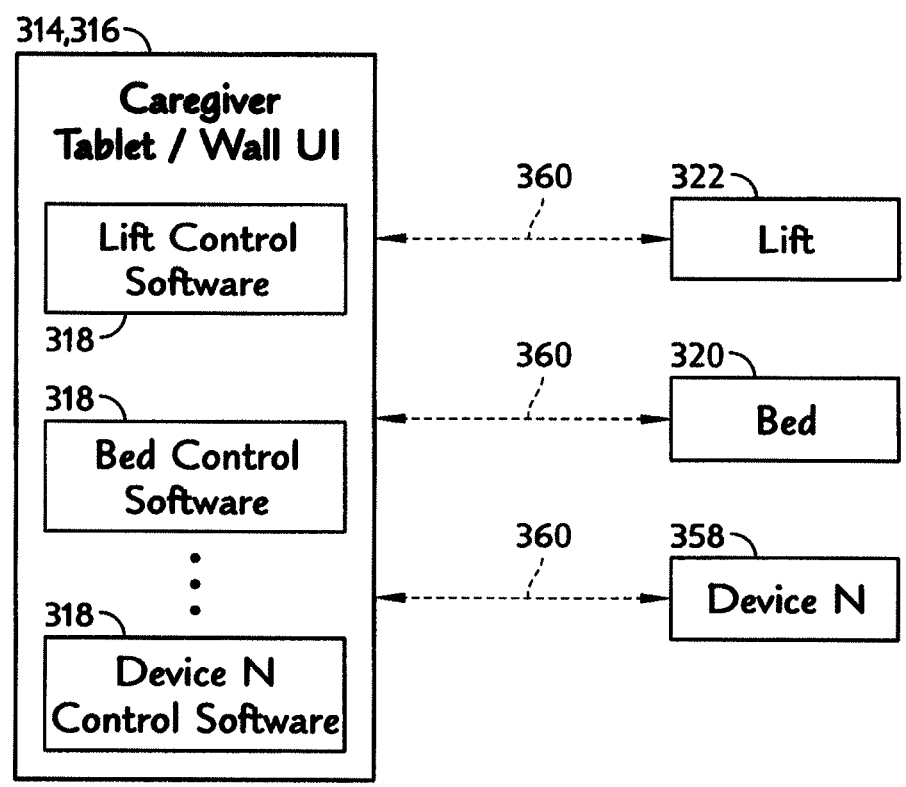
FIG. 8 is a diagrammatic view showing that after application software is loaded into the universal caregiver interfaces, the universal caregiver interfaces communicate command signals to, and received feedback signals from, the patient care devices which, in the illustrative example, include a lift and a bed.

Referring now to FIG. 8, in some embodiments, after application software 318 is received by either or both of interfaces 314, 316 and stored therein, interfaces 314, 316 control the associated patient care devices, such as bed 320, lift 322, and generic patient care device N 358 in the illustrative example, via wireless signals that are sent directly from interfaces 314, 316 to the patient care devices as indicated diagrammatically with dashed double headed arrows 360. Thus, for patient care devices having wireless communication capability, interfaces 314, 316 control such patient care devices without involving server 312, WAP's 330 and communication links 328, 328' in the communication path in some embodiments.

In some embodiments, interface 316 continues to store the application software 318 in its memory even when the caregiver leaves the patient room. Then, when the caregiver returns to the room, a pairing operation is undertaken by the caregiver to link the interface 316 with the patient care devices 358 in the room. Examples of the pairing operation include bumping the interface 316 against the patient care device with which to pair or via manipulating user inputs on interface 316 to initiate the pairing operation. Near field communication (NFC) technology is also within the scope of this disclosure for accomplishing the pairing operation. By using NFC technology, interfaces 314, 316 pair with patient care devices when brought within a short distance (e.g., 3 feet) of each other. In some embodiments, the pairing operation occurs via commands sent by server 312 in response to the presence of interface 316 being sensed in the patient room. However, in that scenario, server 312 does not need to send application software 318 to interface 316 for patient care devices that have remained in the room because interface 316 already has the software 318 stored therein.

According to this disclosure, the default screen that is shown on interface 316 varies depending upon the caregiver's location within a healthcare facility. For example, in some embodiments, the default screen includes patient data, such as heart rate data and respiration rate data, when the caregiver is initially located by the RTLS in the patient room with the patient. The default screen that is shown on interface 316 changes to a previous radiological image or a current radiological image when the caregiver is located by the RTLS in a radiology portion of the healthcare facility with the patient. The default screen that is shown on interface 316 changes to laboratory test results when the caregiver is in a laboratory testing portion of the healthcare facility with the patient. In some embodiments, the default data displayed on interface 316 is filtered based on the caregiver's role. Thus, a doctor's interface 316 displays data that is different than the data displayed on a nurse's interface 316 in some embodiments.

In some embodiments, the default screen shown on interface 316 at some locations in the healthcare facility is the same as the default screen shown on interface 314. In other locations or in other embodiments, the default screen shown on interface 316 at some locations in the healthcare facility is different than the default screen shown on interface 314.

Figure 9:
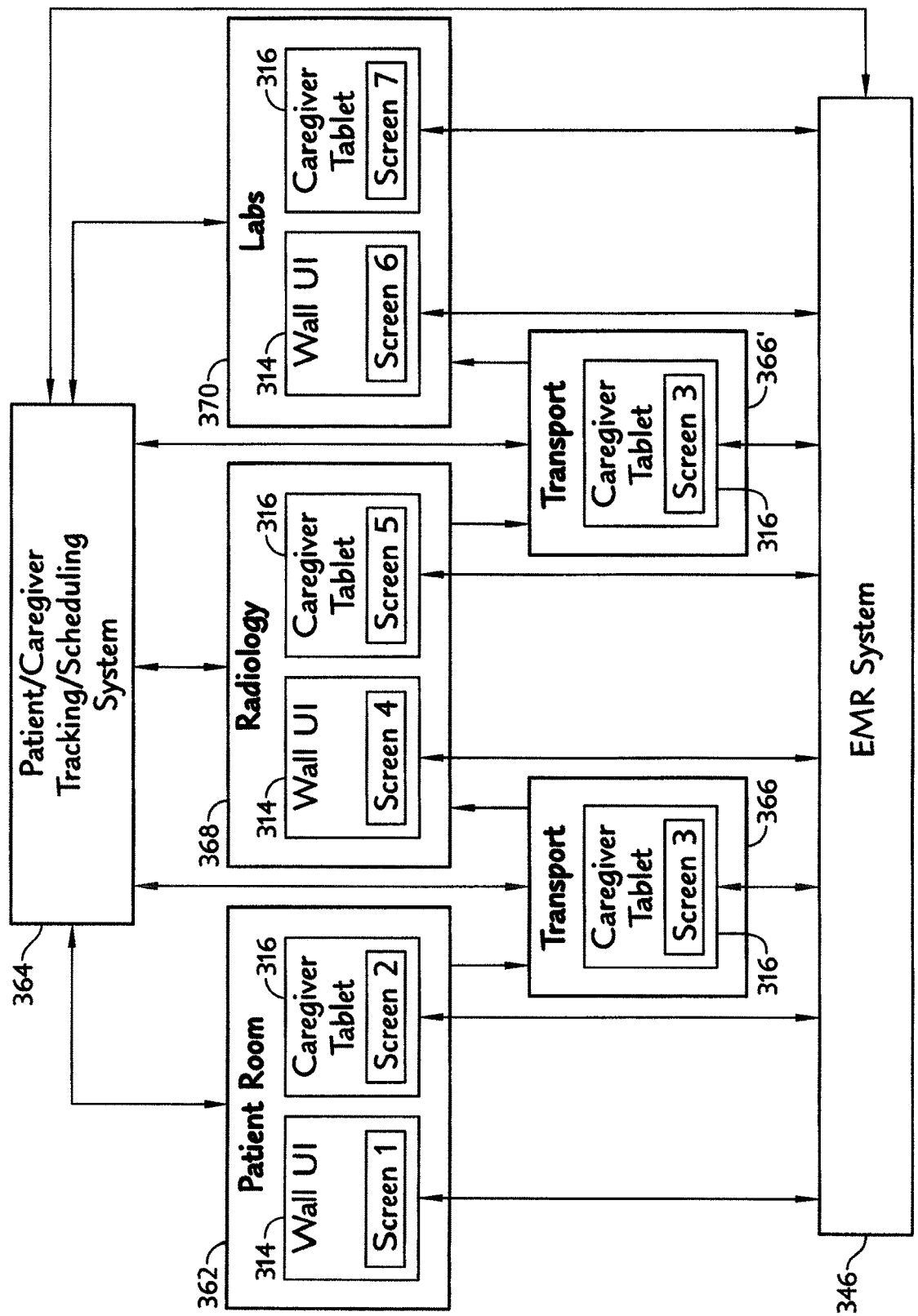
FIG. 9 is a diagrammatic view showing wall-mounted universal caregiver interfaces having display screens that are different based on their location in the healthcare facility and showing that screens of the tablet computer carried by the caregiver varying from one screen to another as the tablet computer is transported from one location to another within the healthcare facility.

FIG. 9 shows this latter scenario diagrammatically. More particularly, in FIG. 9, when a patient and caregiver are located in a patient room interface 314 has a default screen 1 and interface 316 has a default screen 2. An RTLS such as a patient or caregiver tracking or scheduling system 364 is shown diagrammatically in FIG. 9 and monitors the location of patients and/or caregivers within the healthcare facility. Thus, the default screen of interfaces 314, 316 changes based on caregiver location in some embodiments. Alternatively or additionally, the default screens change based on a patient's schedule. Thus, the default screen changes on interfaces 314, 316 occur at preprogrammed times in some embodiments.

When the caregiver and patient exit patient room 362 during transport of the patient to another location in the healthcare facility, as indicated at block 366, the caregiver's interface 316 switches to a default screen 3. In the illustrative example, when the patient and caregiver arrive at radiology 368, the interface 314 in radiology 368 brings up a default screen 4 and the caregiver's interface 316 switches to a default screen 5. When the caregiver exits radiology with the patient to transport the patient to another portion of the healthcare facility, as indicated by block 366' the caregiver's interface 316 reverts back to default screen 3. When the patient and caregiver arrive at a laboratory 370, the interface 314 located in the laboratory 370 brings up a default screen 6 and the caregiver's interface 316 displays a default screen 7.

At least some of the data shown on the various default screens (e.g., screens 1-7 in FIG. 9) is provided by the EMR system 346 of the healthcare facility in the illustrative example. Other data shown on the various default screens is provided by the patient care devices located in the patient room 362, radiology 368, and the laboratory 370. The data shown on screen 3 during transport 366, 366' includes basic information about the patient, such as patient name and the most recent vital sign readings for the patient in some embodiments. In some embodiments, notes about the patient, such as a patient's allergies, are also shown on screen 3 in some embodiments. In some embodiments, default screens 1-7 do not appear on respective interfaces 314, 316 unless a caregiver enters commands on interfaces 314, 316 to bring up the default screens 1-7 at the various locations.

In the illustrative embodiments shown in FIGS. 7-9 interface 316 comprises a tablet computer. According to variant embodiments contemplated by this disclosure, interface 316 comprises a wireless communication device, such as those discussed above in connection with block 350 of FIG. 1, and/or comprises a graphical user interface (GUI) of one of the patient care devices located in the room. For example, a GUI of bed 320 operates as interface 316 in some embodiments. That is, the GUI of bed is able to operate the other patient care devices located in the patient room based on application software 318 for the other patient care devices that is sent to bed 320 by server 312. In some variant embodiments, a personal computer located in the patient room serves as interface 314. The discussion above of the features and functions of interfaces 314, 316 is equally applicable to each of the variant embodiments just mentioned.

In some embodiments, interfaces 316 are also possessed by patients and bed 320 connects to these interfaces 316, which may comprise a patient's own smart device such as an iPhone or iPad, for example. Alternatively or additionally, these types of patient controlled interfaces 316 are connected to one server 312 and the bed 320 connects to another server, such as a nurse call server or bed data management server (e.g., the servers of a SmartSync™ system marketed by Hill-Rom Company, Inc.). The two servers then operate to convey messages between the patient controlled interfaces 316 and associated beds 320. Thus, a patient uses their interface 316 to make a request and the requests are relayed through the first server to the second server. In some instances, the requests are relayed by the second server to a caregiver or, more particularly, to a wireless communication device (e.g., interface 316) assigned to the caregiver. The patient request may be related to ice, pain level, food or drink, for example, or may simply be requesting that a caregiver come to the patient's room for some other reason. In some embodiments, the patient controlled interfaces 316 receive application software 318 and have all of the other functionality of interfaces 316 discussed throughout this disclosure. Thus, the patient controlled interface 316 serves as a patient controller for bed 320 and/or other patient care devices 358, and serves as a communication device for communicating with assigned caregivers. To reiterate, such patient controlled interfaces 316 are the patient's own device brought from home to the healthcare facility in some embodiments.

Based on the foregoing, it will be appreciated that the present disclosure contemplates the following features and functions of a system 310 of a healthcare facility:

interfaces 314, 316 have wired or wireless connectivity to patient care devices (e.g., devices 320, 322, 324) in a patient room to permit device communication and data exchange within the room;

interfaces 314, 316 act as a gateway to the larger enterprise system (e.g., network 326) of the healthcare facility;

by having the ability to control multiple patient care devices with interfaces 314, 316, installation and configuration costs is reduced because interfaces 314, 316 act as a common mechanism to control devices in a patient room and throughout the healthcare facility;

interfaces 314, 316 are usable to initiate medication delivery to a patient;

interfaces 314, 316 document the starting and giving of medication to the patient and provides such information to the EMR system 346 of the healthcare facility;

interfaces 314, 316 receive orders (e.g., physician orders) to notify a caregiver to deliver medication to the patient and the caregiver is able to act on the order received at interfaces 314, 316;

caregivers spend less time trying to find physician's orders because they are delivered to interfaces 314, 316, caregivers spend less time setting up patient care devices to carry out the orders, and caregivers spend less time documenting the carrying out and the completion of the orders;

interfaces 314, 316 display the appropriate patient-related data for viewing by caregivers based on caregiver location and assigned patient(s);

patient-related data is pushed to one or more of the interfaces 314, 316 located closest to the assigned caregiver;

in some embodiments, interfaces 314, 316 only display data if and when a caregiver requests the data to be shown using inputs of interfaces 314, 316;

patient-related data is pushed to wireless communication devices 350 and to interfaces 316 of a patient's assigned caregivers;

patient-related data is removed from interfaces 314, 316 and wireless communication devices 350 when the caregiver leaves the patient room;

patient-related data is removed from interfaces 314, 316 and wireless communication devices 350 when the caregiver reaches a predetermined distance away from interfaces 314, 316 and devices 350;

interfaces 314, 316 are used to control multiple devices and environment settings including, but not limited to, control of room temperature, lights, blinds, patient lifts, beds, pumps, etc.;

interchangeable access to application software 318 is provided using a smart phone, tablet, wall mounted display, in-room computer or embedded medical device user interface;

one interface 314, 316 is able to control multiple aspects or device in the patient environment;

interfaces 314, 316 coordinate controls across multiple devices using application software 318;

interfaces 314, 316 simplify control of the patient environment by providing a single interface to control multiple devices;

interfaces 314, 316 simplify caregiver workflows by allowing access to devices within system 310 from multiple user interface displays;

interfaces 314, 316 simplify caregiver workflows by coordinating control of multiple devices simultaneously;

interfaces 314, 316 display the appropriate patient's data at the appropriate locations at the appropriate time based on a patient schedule or caregiver proximity;

the patient's data is displayed on one or more interfaces 314, 316 in close proximity to the patient;

the patient's data is displayed on one or more interfaces 314, 316 at the location where the patient is assigned to be (e.g., patient room, radiology, etc.);

the patient's data is displayed on the caregiver's mobile device 350 or interface 316 during transport;

the data displayed to the caregiver is altered based on the caregiver's role or specialization;

the full set of patient and device data is pushed to interfaces 314, 316 but the view is filtered based on the patient's assigned environment (e.g., patient room, radiology, labs, etc.);

a subset of patient and device data is pushed to interfaces 314, 316 based on the patient's assigned environment;

the caregiver's view of data on interfaces 314, 316 automatically transitions based on proximity to patient environment type;

the caregiver is able to request specific view of the patient-related data during each step of the patient's stay in the healthcare facility or after a patient has completed a step;

interfaces 314, 316 operate as a wireless master station for controlling devices in a patient room;

the wireless technology is different for interfaces 314, 316 and for the devices in some embodiments;

interfaces 314, 316 link with devices automatically or by pairing or by use of any other link/unlink method;

linking/unlinking of devices and interfaces 314, 316 reduces errors and improves usability of the devices in a healthcare facility;

interfaces 314, 316 reduce the number of interfaces that caregivers need to access;

device costs are reduced for devices made with no user inputs because interfaces 314, 316 are used to control the devices;

interfaces 314, 316 serve as masters for communication and data capture for multiple devices;

one or more of interfaces 314, 316 are not only a screen and touch point for caregivers to document, they also serve as a data capture hub;

one or more of interfaces 314, 316 centralizes patient care and data and communication capture;

in some embodiments, interfaces 314, 316 use multiple association technologies to associate multiple patient care devices substantially simultaneously;

interfaces 314, 316 connect different devices with each other within the room;

interfaces 314, 316 are the communication hub in the room and are able to differentiate one connected device from another;

one or more of interfaces 314, 316 transmit data to a COW, iPad, iPhone and other wireless devices 350;

interfaces 314, 316 facilitate the linkage of data such as lift usage and lift location in combination with a patient bed;

interfaces 314, 316 control any product in a room such as beds, lifts, pumps and other medical devices.

As mentioned above, in some embodiments, bed 320 includes a GUI that serves as interface 316. Thus, application software 318 is downloaded to the circuitry of bed 320 from one or more servers, such as servers 312, 346, or from one or more other servers of network 326. According to this disclosure, the Internet is considered to be a part of network 326 in some embodiments and therefore, web-based applications are accessible for downloading to bed 320 using the interface 316 of bed 320. The applications are accessible using browser software stored in the circuitry of bed 320, for example. In some embodiments, the circuitry of bed 320 includes a Universal Serial Bus (USB) to Ethernet interface for direct access to the hospital intranet and/or Internet 326. Once the web-based applications are downloaded, the circuitry of bed 320 executes the application under the direction of the user who views the software features and functionality using the GUI or interface 316 of bed 320.

In some contemplated embodiments, the circuitry of bed 320 is programmed so as to limit the user from accessing general Internet sites or applications by requiring the user to select from a list of approved web applications such as by selecting from a menu listing or from icons that correspond to the approved web-based applications. In another example, a set of tabs that, when selected, link to pre-approved web applications are shown on the GUI of bed 320 for selection by the user. Limiting access to the software applications available from the healthcare facilities' network 326 is accomplished in a similar manner in some embodiments. It is contemplated by this disclosure that application software for the EMR system 346 is among the pre-approved web applications for bed 320. Once downloaded and executed on bed 320, the EMR software operates the same as if it were being executed and viewed on an EMR computer.

In some embodiments, the circuitry of bed 320 is configured with an authentication software module that is executed prior to the user being permitted access to any or all web sites or applications or to communicate with and/or control devices 314, 316, 350, 324, 336, 338, 340, etc. using bed 320. In other embodiments, the authentication software module is stored in server 312 or some other remote computer device. The discussion below refers to devices 314, 316 (e.g., those not included as part of bed 320) as being the devices authenticated by the authentication software module of bed 320. However, this discussion is equally applicable to other devices such as those discussed herein with which bed 320 interacts.

A number of ways to accomplish authentication of third party devices and software is contemplated by this disclosure. A first is serial number approval. In this method, a list of serial numbers is maintained in a database, such as in a database of the circuitry of bed 320 or in a remote server of network 326 with which bed 320 communicates. Each approved device 314, 316 (when not included as part of bed 320) and/or software application is provided with a serial number. When the device 314, 316 establishes communication with circuitry of bed 320 or when the software application is downloaded to bed 320, the associated serial number of the device 314, 316 or software application, is provided to the circuitry of bed 320 which, in turn, verifies that the serial number is valid. In some embodiments, the device 314, 316 or software application also provides the bed with other device specific or software specific information (e.g., manufacturer ID data, programming entity ID data, device model number, software version number, device ID data, etc.) and the bed also verifies that additional information prior to permitting use of the device 314, 316 or software application with bed 320.

Another example of a software implemented authentication method is secure certificate exchange. According to this method, secure digital certificates are obtained from a Certificate Authority (CA), stored in circuitry of bed 320, and shared with authorized device manufacturers and/or software content providers. The digital certificate is embedded in the device transmission and/or software downloads such that, for example, the certificate information is able to be determined or queried by the bed 320. The bed 320 validates the certificate information to ensure that the device or software is approved for us with the bed 320.

Yet another example of a software implemented authentication method is use of an approved Dynamic Link Library (DLL). In this method, a secure DLL file is created by the manufacturer of bed 320 and is provided to authorized third party device manufacturers and/or software providers. Bed 320 then interrogates the third party device or software for the DLL file prior to allowing the device or software to operate with the bed 320. It is contemplated that, in some embodiments, bed 320 runs a check to confirm that the DLL file has not been tampered with prior to validating the DLL file of the device or software.

In another embodiment, the third party device or software is integrated into or included with the bed 320 such that validation is accomplished ahead of time (e.g., pre-authenticated), such as prior to manufacture or prior to use of the bed 320 in a healthcare facility. The validation that is undertaken ahead of time may be accomplished by any of the validation methods described above, if desired, or by simply installing the software on the bed during manufacture, retrofit, or upgrade so that it is ready to use by the end user. Thus, it should be appreciated that the manufacturer of bed 320 is able to purchase the devices or software from a third-party manufacturer and provide it as an integrated feature or component of bed 320.

As mentioned above, the validation software module is executed by a remote server, such as server 312, rather than on bed 320 in some embodiments. In such embodiments, bed 320 forwards to the remote server information regarding the device(s) 314, 316 attempting to communicate with bed 320 or information regarding the software which is sought to be downloaded to bed 320. The remote server then validates the device(s) and/or software remotely and communicates the validation back to bed 320 which then accepts the software download and/or device 314, 316 pairing with the bed 320 assuming the device(s) and/or software was validated by the remote server. This remote validation method allows for a more centralized approach and provides for an easier way to keep up to date the approved third-party devices and/or software with which bed 320 is able to operate.

According to this disclosure, authentication of different software applications is accomplished via different ones of the authentication methods described above. All permutations and combinations are intended to be within the scope of this disclosure in this regard. Thus, it is within the scope of this disclosure for one or more software applications to be authenticated using serial number approval, one or more others to be authenticated using secure certificate exchange, one or others to be pre-authenticated, and one or more of the others to be authenticated using dynamic link library (DLL). Of course, embodiments using just two or three of these four types of authentication are contemplated.

According to this disclosure, the main functionality of bed 320 takes process priority over the functionality of third party devices and/or software. So bed functions (e.g., moving frame sections of bed 320, inflation control of a mattress of bed 320, etc.) have higher process priority and the third party devices and software applications have lower process priority. Thus, this disclosure contemplates prioritized and filterable message queues which prevent third party devices and software applications from taking precedence over critical bed functionality. In some embodiments, bed 320 includes a publish/subscribe engine that is based on priority message queues. That is, the interface between bed 320 and the third party devices and software applications make use of message queues for communication. In one implementation, the Microsoft® Concurrency and Coordination Runtime (CCR) and/or the XCoordination App Spaces library is used. By using a publish/subscribe mechanism with the third party application process space, the third party devices and software applications are able to safely and effectively receive bed related information and/or communicate with the critical functions (i.e., main functions) of bed 320.

Although certain illustrative embodiments have been described in detail above, variations and modifications exist within the scope and spirit of this disclosure as described and as defined in the following claims.

The invention claimed is:

1. A system comprising
    a remote server, wherein the remote server is part of a network and located remotely from a patient room,
    a patient support system including first communications circuitry in electrical communication with the remote server and second communications circuitry, and
    a mobile computing device, the mobile computing device including
    first communication circuitry for communicating directly with the remote server and
    second communication circuitry capable of communicating with the second communications circuitry of the patient support system,
    the mobile computing device, when paired with the patient support system,
    operable to receive a first signal from the patient support system,
    establish a one-to-one communications link with the second communications circuitry of the patient support system,
    control the patient support system, and transmit to the remote server a second signal indicative of the identity of the patient support system which the mobile device is currently paired, and transmit information received from the patient support system directly to the remote server, wherein the mobile computing device is operable of being selectively paired with different patient support systems, wherein the patient support system includes a first controller operable to communicate data to the remote server, the data communicated to the remote server being processed by the remote server to reduce the processing load of the controller of the first patient support system, and upon completion of the processing of the data, the remote server is operable to return the results of the processed data to the first controller of the first patient support system, and wherein the remote server processes the second signal and transmits the information from the patient support system to a hospital information system.

2. The system of claim 1, wherein the mobile computing device includes operational circuitry used by a caregiver to enter patient related information.

3. The system of claim 2, wherein the mobile computing device associates the patient related information with the information from the patient support system and transmits the associated data to the remote server.

4. The system of claim 1, wherein the remote server transmits instructions intended for the patient support system to the mobile computing device.

5. The system of claim 4, wherein the mobile computing device is configured to prompt a user to accept pairing with the patient support system and to cause the instructions from the remote server intended for the patient support system to be transmitted by the mobile computing device to the patient support system.

6. The system of claim 1, wherein the patient support system includes a user interface and wherein the mobile computing device is configured to access the remote server to access functionality of the patient support system that is not accessible from the user interface, the functionality accessible from the mobile computing device being dependent on the authority level of the mobile computing device.

7. The system of claim 1, further comprising a remote computer device in communication with the patient support system, the patient support system having circuitry operable by a user to obtain at least one software application from the remote computer device, and an authentication software module that verifies that the at least one software application is authorized for use on the patient support system, the at least one software module being unusable on the patient support system until verification has occurred.

8. The system of claim 1, wherein the first and second communications circuitry comprise wireless communication systems.

9. The system of claim 8, wherein the remote server is in electrical communication with the patient support system through physical communications connection.

10. The system of claim 9, wherein the first communication system is a 3G communication system.

11. The system of claim 10, wherein the second communications system utilizes the Bluetooth communications protocol.

12. The system of claim 11, wherein the electrical connection is an Ethernet connection.

13. The system of claim 1, wherein the mobile computing device is associated with expanded functionality to perform maintenance and diagnostic operations on the patient support system.

14. The system of claim 1, wherein the remote server is operable to send a software update to the patient support system via the mobile device.

15. The system of claim 14, wherein a user may review and authorize the software update to the patient support system via the mobile computing device.

16. The system of claim 1, wherein the mobile computing device receives the signal from the patient support system when the patient support system is within a range of communication of the mobile computing device, and the one-to-one communications link with the second communications circuitry of the patient support system is established after an user is prompted to accept pairing with the patient support system.

17. The system of claim 1, wherein the one-to-one communications link with the second communications circuitry of the patient support system is established by physically contacting the mobile computing device with the patient support system.

18. The system of claim 1, wherein the patient support system comprises is a first patient support system that includes a first controller, the first controller operable to control functionality of the first patient support system.

19. The system of claim 18, wherein the system further comprises a second patient support system including a second controller, the second controller operable to control functionality of the second patient support system, wherein the second controller of the second patient support system is operable to communicate data to the remote server, the data communicated to the remote server being processed by the remote server to reduce the processing load of the second controller of the second patient support system, and upon completion of the processing of the data, the remote server is operable to return the results of the processed data to the second controller of the second patient support system.

20. The system of claim 19, wherein the first controller and the second controller transfer data to the remote server which is associated with non-critical functionality of the first patient support system and the second first patient support system to reduce the processing load on the controllers.

21. The system of claim 20, wherein the mobile computing device is paired with the first patient support system or the second patient support system.

22. The system of claim 21, wherein the mobile computing device acts as a user interface for the patient support system with which the mobile computing device is paired.

23. The system of claim 1, wherein the mobile device is operable to pair with a beacon, the beacon operable to transmit a signal to the mobile computing device indicative of the patient support system.

* * * * *